US010961543B2

(12) United States Patent
Koch et al.

(10) Patent No.: US 10,961,543 B2
(45) Date of Patent: Mar. 30, 2021

(54) TONOPLAST PROTON/SUGAR ANTIPORTER PROTEINS AND THE USE THEREOF TO INCREASE THE SACCHAROSE CONCENTRATION IN A SACCHAROSE STORAGE ORGAN OF PLANTS

(71) Applicants: KWS SAAT SE & CO. KGAA, Einbeck (DE); SÜDZUCKER AG, Mannheim (DE)

(72) Inventors: Wolfgang Koch, Einbeck (DE); Norbert Sauer, Erlangen (DE); Petra Wirsching, Fürth (DE); Benjamin Pommerrenig, Halberstadt (DE); Ekkehard Neuhaus, Kaiserslautern (DE); Benjamin Jung, Fischbach (DE); Ulf-Ingo Flügge, Cologne (DE); Frank Ludewig, Cologne (DE); Nicole Lenzen, Düren (DE); Irene Marten, Würzburg (DE); Rainer Hedrich, Würzburg (DE); Alexander Schulz, Würzburg (DE)

(73) Assignees: KWS SAAT SE & CO. KGAA, Einbeck (DE); SÜDZUCKER AG, Mannheim (DE)

(*) Notice: Subject to any disclaimer, the term of this patent is extended or adjusted under 35 U.S.C. 154(b) by 234 days.

(21) Appl. No.: 15/303,488

(22) PCT Filed: Apr. 10, 2015

(86) PCT No.: PCT/DE2015/000170
§ 371 (c)(1),
(2) Date: Oct. 11, 2016

(87) PCT Pub. No.: WO2015/154741
PCT Pub. Date: Oct. 15, 2015

(65) Prior Publication Data
US 2018/0080037 A1 Mar. 22, 2018

(30) Foreign Application Priority Data
Apr. 11, 2014 (DE) .................. 10 2014 005 337.7

(51) Int. Cl.
| C12N 15/82 | (2006.01) |
| C12Q 1/68 | (2018.01) |
| C07K 14/415 | (2006.01) |
| C12Q 1/6895 | (2018.01) |

(52) U.S. Cl.
CPC ........ *C12N 15/8245* (2013.01); *C07K 14/415* (2013.01); *C12Q 1/6895* (2013.01); *C12Q 2600/13* (2013.01)

(58) Field of Classification Search
None
See application file for complete search history.

(56) References Cited

U.S. PATENT DOCUMENTS

| 5,954,357 | A | 9/1999 | Golling | |
| 6,007,086 | A | 12/1999 | Hopkins | |
| 6,299,192 | B1 | 10/2001 | Bryce | |
| 2003/0047910 | A1 | 3/2003 | Golling | |
| 2003/0236208 | A1* | 12/2003 | Kmiec | ................. C12N 15/102 514/44 R |
| 2007/0164523 | A1 | 7/2007 | Yoshino | |
| 2011/0193323 | A1 | 8/2011 | Rivard et al. | |
| 2012/0211969 | A1 | 8/2012 | Walker | |

FOREIGN PATENT DOCUMENTS

| KR | 20110085729 A | 7/2011 |
| KR | 20110085732 A | 7/2011 |
| WO | 2008/070179 A2 | 6/2008 |
| WO | 2010/072210 A1 | 7/2010 |
| WO | 2011/120549 A1 | 10/2011 |

OTHER PUBLICATIONS

Schulz et al., 2011, The Plant Journal 68: 129-136.*
Beta vulgaris, Locus_1975_Transcript_13/21, mRNA sequence, NCBI/GenBank accession No. JP489056, published Oct. 17, 2012.*
Keskin et al., 2004, Protein Science 13: 1043-1055.*
Thornton et al., 2000, Nature Structural Biology, structural genomic supplement, Nov. 2000: 991-994.*
Guo et al., 2004, Proceedings of the National Academy of Sciences USA 101: 9205-9210.*
Hedrich et al., 2015, Current Opinion in Plant Biology 25: 63-70.*
Mutasa-Göttgens et al., 2012, A new RNASeq-based reference transcriptome for sugar beet and its application in transcriptome-scale analysis of vernalization and gibberellin responses, BMC Genomics 2012, 13:99, pp. 1-18, with supplementary material.*
Belladonna KWS variety description, Naktuinbouw (the Netherlands Inspection Service for Horticulture), 2009.*
Endler et al., "Identification of a vacuolar sucrose transporter in barley and *Arabidopsis* mesophyll cells by a tonoplast proteomic approach", Plant Physiology, vol. 141, No. 1, May 2006, pp. 196-207.
International Preliminary Report on Patentability and Written Opinion of the International Searching Authority issued in International Application No. PCT/DE2015/100170 dated Nov. 1, 2016.
International Search Report on Patentability issued in International Application No. PCT/DE2015/100170 dated Sep. 22, 2015.

(Continued)

*Primary Examiner* — Bratislav Stankovic
(74) *Attorney, Agent, or Firm* — Troutman Pepper Hamilton Sanders LLP

(57) ABSTRACT

The invention relates to tonoplast proton/sugar antiporter proteins, more particularly tonoplast proton/saccharose antiporter proteins, the nucleotide sequences which encode them and uses thereof for producing transgenic plants with an increased saccharose concentration. The invention also includes methods for producing transgenic plants with an increased saccharose concentration, methods for increasing the saccharose concentration in plants, and for identifying plants which are suitable for creating a higher saccharose concentration.

9 Claims, 4 Drawing Sheets

Specification includes a Sequence Listing.

(56) References Cited

OTHER PUBLICATIONS

International Search Report on Patentability issued in International Application No. PCT/DE2015/100170 dated Oct. 26, 2015.
Kuhn et al., "Sucrose transporters of higher plants", Current Opinion in Plant Biology, vol. 13, No. 3, Jun. 1, 2010, pp. 287-297.
Ludewig et al., "Role of metabolite transporters in source-sink carbon allocation", Frontiers in Plant Science, vol. 4, 231, Jul. 2, 2013, pp. 1-16.
Wingenter et al., "Increased Activity of the Vacuolar Monosaccharide Transporter TMT1 Alters Cellular Sugar Partitioning, Sugar Signaling, and Seed Yield in *Arabidopsis*", Plant Physiology, vol. 154, No. 2, Oct. 1, 2010, pp. 665-677.
Database EMBL [Online], Oct. 17, 2012 (Oct. 17, 2012), "TSA: Beta vulgaris Locus_1975_Transcript_18121_Confidence_0.269_Length_3084mRNA sequence.", XP002743849, retrieved from EBI accession No. EM_TSA:JP489061 Database accession No. JP489061 sequence.
He Lei, "Physiological Basis of Sucrose Accumulation in Sugarbeet Root", China Master Dissertations Full-test Database. Agricultural Science and Technology Series, D047-97, Mar. 15, 2010.
Martinola et al., "Vacuolar transporters and their essential role in plant metabolism", Journal of Experimental Botany, 2007, vol. 58, No. 1, pp. 83-102.
Neuhaus, "Transport of primary metabolites across the plant vacuolar membrane", FEBS Letters, 2007, vol. 581, pp. 2223-2226.
Wormit et al., "Molecular identification and physiological characterization of a novel monosaccharide transporter from *Arabidopsis* involved in vacuolar sugar transport", The Plant Cell, 2006, vol. 18, pp. 3476-3490.
Reiser et al., "Molecular physiological analysis of the two plastidic ATP/ADP transporters from *Arabidopsis*", Plant Physiology, 2004, vol. 136, pp. 3524-3536.
Leroch et al., "Identification and characterization of a novel plastidic adenine nucleotide uniporter from Solanum tuberosum", The Journal of Biological Chemistry, 2005, vol. 280, No. 18, pp. 17992-18000.
Leigh et al., "Isolation of Vacuoles from Root Storage Tissue of Beta *vulgaris* L.", Plant Physiol., 1976, vol. 58, pp. 656-662.
Schulze et al., "Cold acclimation induce changes in *Arabidopsis* tonoplast protein abundance and activity and alters phosphorylation of tonoplast monosaccharide transporters", The Plant Journal, 2012, vol. 69, pp. 529-541.
Boller et al., "Hydrolytic enzymes in the central vacuole of plant cells", Plant Physiol., 1979, vol. 63, pp. 1123-1132.
Latz et al., "In planta AKT2 subunits constitute a pH and $Ca^{2+}$-sensitive inward rectifying K+ channel", Planta, 2007, vol. 225, pp. 1179-1191.
Beyhl et al., "The foul mutation in the major vacuolar cation channel TPC1 confers tolerance to inhibitory luminal calcium", The Plant Journal, 2009, vol. 58, pp. 715-723.
Yoo et al., "*Arabidopsis* mesophyll protoplasts: a versatile cell system for transient gene expression analysis", Nature Protocols, 2007, vol. 2, No. 7, pp. 1565-1572.
Kodama, "Analytical Methods for genetically modified Maize and Soybean, and Tendency for Interlaboratory Precision in the GM Quantitative Method", 2011, (8), 342-352.

* cited by examiner

| | BvTST1 | AfTMT2 | BvTST2.1 | BvTST2.2 | AfTMT3 | BvTST3 | |
|---|---|---|---|---|---|---|---|
| AfTMT1 | 62%<br>77% | 61%<br>75% | 56%<br>73% | 57%<br>74% | 52%<br>68% | 58%<br>72% | Identity<br>Similarity |
| BvTST1 | | 65%<br>80% | 58%<br>76% | 61%<br>77% | 57%<br>71% | 60%<br>74% | Identity<br>Similarity |
| AfTMT2 | | | 68%<br>84% | 70%<br>84% | 60%<br>75% | 64%<br>77% | Identity<br>Similarity |
| BvTST2.1 | | | | 84%<br>92% | 56%<br>73% | 61%<br>75% | Identity<br>Similarity |
| BvTST2.2 | | | | | 58%<br>75% | 63%<br>76% | Identity<br>Similarity |
| AfTMT3 | | | | | | 60%<br>75% | Identity<br>Similarity |

TONOPLAST PROTON/SUGAR ANTIPORTER PROTEINS AND THE USE THEREOF TO INCREASE THE SACCHAROSE CONCENTRATION IN A SACCHAROSE STORAGE ORGAN OF PLANTS

CROSS-REFERENCE TO RELATED APPLICATIONS

This application is a national phase of International Application No. PCT/DE2015/000170, filed on Apr. 10, 2015, which claims priority to German Patent Application No. 10 2014 005 337.7, filed on Apr. 11, 2014, the disclosures of all of which are incorporated herein by reference in their entirety.

SEQUENCE LISTING

The instant application contains a Sequence Listing which has been submitted electronically in ASCII format and is hereby incorporated by reference in its entirety. Said ASCII copy, created in Aug. 21, 2018, is named KWS_20180822_ST25.txt and is 70,422 bytes in size.

The present invention is in the field of industrial sugar production from crops and relates to the increase of the saccharose yield in agricultural cultivation of crop plants. In particular, the invention relates to tonoplast proton/sugar antiporter proteins, more particularly tonoplast proton/saccharose antiporter proteins and nucleic acids which encode them and the use thereof for increasing the saccharose concentration of a saccharose storage organ of crop plants.

On the one hand, sugar is a collective term for all sweet-tasting mono- and disaccharides, on the other hand, the commercially common name for the disaccharide saccharose. Saccharose is the ordinary household or granulated sugar and is also known as sucrose. Saccharose is a dimer of one molecule of α-D-glucose and β-D-fructose, which are interconnected via an α,β-1,2-glycosidic bond.

Saccharose is formed in plants by means of photosynthesis. The biosynthesis of saccharose takes place in the cytoplasm of plant cells. For this purpose, the two triose phosphates, glyceraldehyde-3-phosphate and dihydroxyacetone phosphate, which arise as the net result in the carbon assimilation of photosynthesis (Calvin cycle), are exported from the chloroplast to the cytosol. In the cytosol of the plant cell the monosaccharides UDP-glucose and fructose 6-phosphate are formed from the triose phosphates. For this purpose, first fructose-1,6-bisphosphate is formed by a condensation reaction between glyceraldehyde-3-phosphate and dihydroxyacetone phosphate. Fructose-1,6-bisphosphate is then to reacted to form fructose-6-phosphate by dephosphorylation. Fructose-6-phosphate can also form glucose-6-phosphate by isomerization, which, after prior isomerization forming glucose-1-phosphate, reacts with uridine triphosphate (UTP) to form uridine diphosphate glucose (UDP-glucose). The subsequent condensation of UDP-glucose and fructose-6-phosphate forming saccharose-6-phosphate is catalyzed by the enzyme saccharose-phosphate synthase. The necessary energy is provided by the elimination of uridine diphosphate (UDP). Finally, the phosphate residue of saccharose-6-phosphate is cleaved in an irreversible reaction by the enzyme saccharose-phosphate-phosphatase so that saccharose is produced. Saccharose is a non-reducing disaccharide and is therefore the most important transport sugar in plants. Saccharose is synthesized new in the leaves of plants and transported via the phloem in the storage organs thereof, where it accumulates in the vacuoles of the plant cells as a nutrient and energy source.

Of importance for the industrial production of saccharose are especially sugar beet (*Beta vulgaris* subsp. *vulgaris*), sugar cane (*Saccharum officinarum*) and sugar palm (*Arenga pinnata*, syn.: *Arenga saccharifera* Labil., mainly in Indonesia). In smaller amounts, saccharose is also obtained from the juice of sugar maple (*Acer saccharum*). These plants are used for the production of saccharose because of their exceptionally high saccharose content.

In sugar cane there are sugars—mostly saccharose—in a proportion of usually 10 to 20% in the marrow of the plant (the saccharose storage organ thereof). The cane sugar is obtained by crystallization and refining of the plant juice obtained through juicing.

Sugar beet is a biennial plant, which builds up a sugar supply in the beet body in the first year which is used as food of the flowering plant in the 2nd year. Sugar is usually produced from sugar beet chips in an extraction process with water. The extract may then be treated with calcium oxide to precipitate the plants acids such as oxalic acid or tartaric acid and the proteins. The excess lime is separated by introducing carbon dioxide. Through the subsequent evaporation of the water from the sugar solution in a vacuum, a syrupy solution is obtained. The crystallizing sugar is separated from the remaining brown syrup by centrifugation. The residue, the molasses, is used as cattle feed or is used for alcoholic fermentation. Purification of the sugar (refining) is carried out by recrystallization, filtration and by evaporation in a vacuum.

Through decades of efforts in cultivating saccharose-storing plants substantial increases in yield of the saccharose storage organ and the saccharose concentration could be achieved. For example, in sugar beet varieties currently grown for sugar production, the saccharose concentration of the beet body is about 15 to 20% by weight, based on the fresh weight of the root body. However, the saccharose concentrations obtained are still not satisfactory.

The object of the present invention was therefore to provide plants with a higher saccharose concentration and to find methods by which the saccharose concentration of plants, especially of sugar cane and sugar beet, can be increased.

The international application published as WO 2010/072210 A1 discloses a method for increasing the saccharose yield in the agricultural cultivation of sugar beet. In said method, sugar beet or sugar cane plants are used whose genetic makeup is aimed at reducing the enzymatic activity of an invertase. For this purpose, a nucleic acid which is suitable in a plant cell to reduce the enzymatic activity of an invertase, is used to form a saccharose storage organ of a plant, wherein the saccharose concentration is increased compared with the saccharose concentration of a non-modified control saccharose storage organ of the same genotype in a comparable stage of development.

Plant vacuoles play a central role in the long- or short-term storage of sugars, because the vacuole as organelle occupies a volume of about 90% in a photosynthetically active plant cell (Martinola, E. et al. (2007) "Vacuolar transporters and their essential role in plant metabolism", J. Exp. Bot. 58: 83-102). Due to their size vacuoles are therefore of immense importance for storing sugars (Neuhaus, H. E. (2007) "Transport of primary metabolites across the plant vacuolar membrane", FEBS Lett 581: 2223-2226). Storage tissues such as the taproot of sugar beet (*Beta vulgaris*) and the marrow of sugar cane (*Saccharum officinarum*) accumulate large amounts of saccharose in the vacuoles of the cells of their storage organs to use them as a source of energy for their plant metabolism.

In various monocotyledonous and dicotyledonous plants such as *Medicago* (identification no. AC131026), *Vitis vinifera* (identification no. AAX47312) and rice (*Oryza sativa*; identification no. Os02g13560). Proteins were discovered, which are responsible for the sugar transport from the cytoplasm of the plant cell into the vacuole thereof. In the plant *Arabidopsis*, a gene has been identified, whose protein product is a sugar transporter, which is localized in the vacuolar membrane of photosynthetically active cells and can import glucose from the cytosol into the vacuole (Wormit, A. et al. (2006) "Molecular identification and physiological characterization of a novel monosaccharide transporter from *Arabidopsis* involved in vacuolar sugar transport", Plant Cell 18: 3476-3490). This transport protein known as tonoplast monosaccharide transporter (TMT) is localized in the membrane of the vacuole, the tonoplast. The tonoplast monosaccharide transporter (TMT) protein comprises three isoforms in *Arabidopsis thaliana*, which are called AtTMT1, AtTMT2 and AtTMT3. The genes for AtTMT1 and AtTMT2 have a tissue- and cell type-specific expression patterns, whereas the AtTMT3 gene is expressed only very weakly. Via TMT gene knockouts it could be shown that the so modified plants accumulated significantly less glucose and fructose in their vacuoles compared to wild-type plants. With regard to the accumulation of saccharose, however, no differences between the wild-type plants and the TMT gene knockouts were detected.

The tonoplast monosaccharide transporter TMT1 from *Arabidopsis thaliana* was characterized electrophysiologically as a proton-driven glucose and saccharose antiporter, which transports glucose and saccharose at approximately the same specificity through the vacuolar membrane (Schulz, A. et al. (2011) "Proton-driven sucrose symport and antiport are provided by the vacuolar transporters SUC4 and TMT1/2", The Plant Journal 68: 129-136). In the same article the saccharose transport protein SUC4 of *Arabidopsis thaliana* is characterized as proton/saccharose symporter, which should be also localized in the vacuolar membrane.

The international application published as WO 2011/120549 A1 discloses that the seed yield can be increased, the protein and oil content of the seeds can be increased or the early growth of monocotyledonous or dicotyledonous plants can be promoted by overexpression of the tonoplast monosaccharide transporter AtTMT1 in plants. An accumulation of saccharose in a storage organ is not disclosed.

Against this background, the object underlying the present invention has been achieved by identifying the proteins responsible for the import of sugar into the vacuole of taproot cells of sugar beet, in particular the protein responsible for the import of saccharose into the vacuoles of the taproot cells of sugar beet, which is specific for saccharose. With the identification of these proteins, in particular with the identification of this first saccharose-specific tonoplast proton/sugar antiporter protein and the nucleotide sequences encoding these proteins culturing and/or molecular genetic methods for increasing the saccharose concentration in plants and therefore also plants with a higher saccharose concentration are provided.

According to a first aspect, the invention relates to a nucleic acid molecule encoding a tonoplast proton/sugar antiporter protein. Preferably, the nucleic acid molecule encodes a tonoplast proton/sugar antiporter protein that is specific for saccharose. Hereinafter, such a proton/sugar antiporter protein that is specific for saccharose, is referred to also as proton/saccharose antiporter protein.

According to a second aspect, the invention relates to a recombinant gene comprising a nucleic acid molecule according to the first aspect or a nucleic acid molecule having a nucleotide sequence which encodes a tonoplast proton/sugar antiporter protein, preferably a tonoplast proton/saccharose antiporter protein. The nucleic acid molecule may be operatively linked to at least one regulatory element.

According to a third aspect, the invention relates to a vector or mobile genetic element, comprising a nucleic acid molecule according to the first aspect or a recombinant gene according to the second aspect.

According to a further aspect, the invention relates to a eukaryotic host cell or a prokaryotic host cell comprising a nucleic acid molecule according to the first aspect, preferably as a transgene, a recombinant gene according to the second aspect, or a vector or mobile genetic element according to the third aspect.

According to a further aspect, the invention relates to a protein which functions as a proton/sugar antiporter, which preferably is specific for saccharose, or preferably as tonoplast proton/saccharose antiporter.

According to a further aspect, the invention relates to a transgenic plant cell comprising a nucleic acid molecule according to the first aspect as a transgene, a recombinant gene according to the second aspect as a transgene, or a vector or mobile genetic element according to the third aspect, and a transgenic plant or parts thereof which comprise at least one such transgenic plant cell.

According to a further aspect, the invention relates to seeds of a transgenic plant according to the preceding aspect, wherein the seeds comprise a nucleic acid molecule according to the first aspect as a transgene, a recombinant gene according to the second aspect as a transgene, or a vector or mobile genetic element according to the third aspect.

According to a further aspect, the invention relates to methods for producing transgenic plants.

According to a further aspect, the invention relates to methods for increasing the saccharose concentration of a saccharose storage organ of a plant.

According to a further aspect, the invention relates to methods for identifying a plant that is suitable to generate an increased saccharose concentration in a saccharose storage organ of the plant.

According to a further aspect, the invention relates to oligonucleotides which are suitable for use as molecular markers for the diagnostic detection of a nucleic acid molecule according to the first aspect.

According to a further aspect, the invention relates to antibodies which are diagnostic of a protein that functions as a tonoplast proton/sugar antiporter, which preferably is specific for saccharose, preferably as tonoplast proton/saccharose antiporter.

According to a further aspect, the invention relates to the use of tonoplast proton/sugar antiporter proteins for increasing the saccharose concentration of a saccharose storage organ of a plant.

Figures 1, 2:
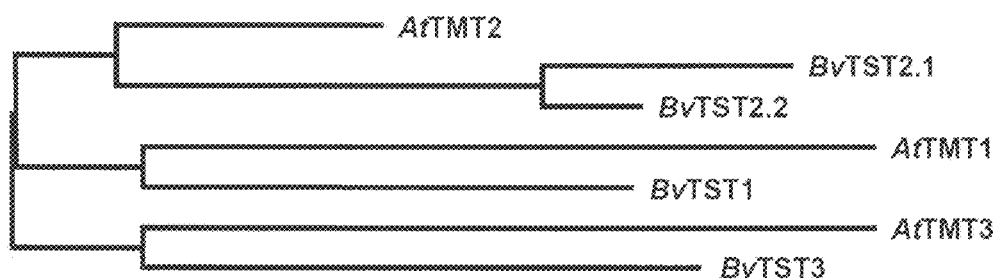
FIG. 1 shows a table indicating the identities and the similarities of the amino acid sequences of the three paralogous tonoplast monosaccharide transporter (TMT) proteins from *Arabidopsis thaliana* with the four paralogous tonoplast sugar transporter (TST) proteins from *Beta vulgaris*.
FIG. 2 shows a cladogram illustrating the phylogenetic relationships of the three paralogous tonoplast monosaccharide transporter (TMT) proteins from *Arabidopsis thaliana* and the four paralogous tonoplast sugar transporter (TST) proteins from *Beta vulgaris*.

The inventors have identified the protein called here BvTST2.1 as one of the quantitatively most abundant proteins of the vacuolar membrane of taproot cells of sugar beet and surprisingly found that the protein BvTST2.1 can import specifically saccharose from the cytosol into the vacuoles of plant cells as tonoplast sugar transporter. Therefore, this protein and proteins with the same function not only represent tonoplast sugar transporters (TST), but are also referred to as tonoplast saccharose transporters or tonoplast proton/saccharose antiporter or tonoplast protons/saccharose antiporter proteins, wherein "Bv" in the abbreviation used herein stands for *Beta vulgaris*, the organism in which this protein was originally identified. The inventors identified the protein BvTST2.1 as a proton/sugar antiporter protein that is highly specific for saccharose and which represents the first known representative of this plant sugar-transporting protein family. In addition, three other paralogous isoforms, BvTST1, BvTST2.2 and BvTST3, which are probably functionally associated with the known TMT proteins from *Arabidopsis*, have been successfully identified.

Based on the identification of this novel, saccharose-specific antiporter, the inventors have also identified the nucleotide sequences encoding the tonoplast proton/sugar antiporter protein and the other isoforms.

Therefore, according to the first aspect, the invention relates to nucleic acid molecules encoding a tonoplast proton/sugar antiporter protein, preferably a tonoplast proton/saccharose antiporter protein.

According to an embodiment, the nucleic acid molecule encoding a tonoplast proton/saccharose antiporter protein comprises a nucleic acid molecule selected from the group:
a) a nucleic acid molecule having a nucleotide sequence according to SEQ ID NO: 2, or a nucleic acid molecule having a nucleotide sequence having an identity of at least 80% to the nucleotide sequence according to SEQ ID NO: 2;
b) a nucleic acid molecule having a nucleotide sequence which is complementary to one of the nucleotide sequences according to a);
c) a nucleic acid molecule that hybridizes with a nucleic acid molecule according to a) or b);
d) a nucleic acid molecule having a nucleotide sequence encoding a polypeptide having an amino acid sequence according to SEQ ID NO: 1, or a nucleic acid molecule having a nucleotide sequence encoding a polypeptide whose amino acid sequence has an identity of at least 80% to the amino acid sequence according to SEQ ID NO: 1; and
e) a nucleic acid molecule having a nucleotide sequence encoding a homolog, analog or ortholog of the polypeptide according to SEQ ID NO: 1.

According to a further embodiment, the nucleic acid molecule encoding a tonoplast proton/sugar antiporter protein comprises a nucleic acid molecule selected from the group:
a) a nucleic acid molecule having a nucleotide sequence according to SEQ ID NO: 4, 6 or 8, or a nucleic acid molecule having a nucleotide sequence having an identity of at least 80% to the nucleotide sequence according to SEQ ID NO: 4, 6 or 8;
b) a nucleic acid molecule having a nucleotide sequence which is complementary to one of the nucleotide sequences according to a);
c) a nucleic acid molecule that hybridizes with a nucleic acid molecule according to a) or b);
d) a nucleic acid molecule having a nucleotide sequence encoding a polypeptide having an amino acid sequence according to SEQ ID NO: 3, 5, or 7, or a nucleic acid molecule having a nucleotide sequence encoding a polypeptide whose amino acid sequence has an identity of at least 80% to the amino acid sequence according to SEQ ID NO: 3, 5 or 7; and
e) a nucleic acid molecule having a nucleotide sequence encoding a homolog, analog or ortholog of the polypeptide according to SEQ ID NO: 3, 5, or 7.

The term "nucleic acid molecule having a nucleotide sequence" comprises not only nucleic acid molecules whose nucleotide sequence consists of the nucleotide sequence then described in more detail, but also nucleic acid molecules which in addition to the nucleotide sequence then described in more detail have at least one nucleotide or nucleotide sequences.

According to an alternative and/or additional embodiment the nucleic acid molecule encodes an amino acid sequence according to SEQ ID NO: 1, 3, 5 or 7. However, the nucleic acid molecule may also encode an amino acid sequence in which at least one amino acid residue of the amino acid sequence has been substituted by an amino acid having similar chemical properties (conservative or semi-conservative amino acid substitution). In a conservative amino acid substitution an amino acid is replaced by another amino acid with similar chemical properties. In a semi-conservative amino acid substitution, an amino acid is replaced by another amino acid having a similar steric conformation. The substitution preferably has no effect on protein function. Examples of amino acid substitutions are Asp and Glu, Leu and Ile, Ala and Val, Arg and Lys, and Phe and Trp.

According to an alternative and/or additional embodiment, the nucleotide sequences of the nucleic acids and/or the amino acid sequences encoded by the nucleotide sequences have an identity of at least 80%, at least 85%, preferably at least 90%, particularly preferably at least 95%, at least 96%, at least 97% or at least 98%, and most preferably of at least 99% to the nucleotide sequence according to SEQ ID NO: 2, 4, 6 or 8 or the amino acid sequence according to SEQ ID NO: 1, 3, 5 or 7.

The term "hybridize" as used herein means hybridizing under conventional conditions, such as described in Sambrook et al. (1989) "Molecular Cloning, A Laboratory Manual" (Cold Spring Harbor Laboratory Press, New York), preferably under stringent conditions. Stringent hybridization conditions are, for example: hybridizing in 4×SSC at 65° C. and followed by multiple washes in 0.1×SSC at 65° C. for a total of about 1 hour. Less stringent hybridization conditions are, for example: hybridizing in 4×SSC at 37° C. and followed by multiple washes in 1×SSC at room temperature. "Stringent hybridization conditions" can also mean: hybridizing at 68° C. in 0.25 M sodium phosphate, pH 7.2, 7% SDS, 1 mM EDTA and 1% BSA for 16 hours and followed by two washes with 2×SSC and 0.1% SDS at 68° C.

For the purposes of the invention, "specific for saccharose" or "highly specific for saccharose" or "saccharose-specific transport" or "saccharose highly specific transport" or "specificity for saccharose" or "saccharose specificity" mean that the specificity of a tonoplast proton/sugar antiporter protein for saccharose over another sugar is at least 5-fold, 10-fold or 15-fold, preferably at least 18-fold, 20-fold, 22-fold, 24-fold, 26-fold or 28-fold, particularly preferably at least 30-fold, at least 31-fold, at least 32-fold, at least 33-fold, at least 34-fold, at least 35-fold, at least 36-fold, at least 37-fold, at least 38-fold or at least 39-fold, and most preferably at least 40-fold higher. Furthermore, this may also mean that the specificity of a tonoplast proton/sugar antiporter protein for saccharose over a monosaccharide such as glucose or fructose is at least 5-fold, 10-fold or 15-fold, preferably at least 18-fold, 20-fold, 22-fold, 24-fold, 26-fold or 28-fold, particularly preferably at least 30-fold, at least 31-fold, at least 32-fold, at least 33-fold, at least 34-fold, at least 35-fold, at least 36 fold, at least 37-fold, at least 38-fold or at least 39-fold, and most preferably at least 40-fold higher.

For the purposes of the invention, a "homolog" means a protein of same phylogenetic origin, an "analog" means a protein which carries out the same function, but has a different phylogenetic origin, and an "ortholog" means a protein from another species, which carries out the same function.

According to the second aspect, the invention relates to a recombinant gene comprising a nucleic acid molecule according to the first aspect or a nucleic acid molecule having a nucleotide sequence which preferably encodes a tonoplast proton/saccharose antiporter protein. The nucleic acid molecule may be operatively linked to at least one regulatory element.

A "regulatory element" means nucleotide sequences which are not part of the protein-encoding nucleotide sequence, but mediate the expression of the protein-encoding nucleotide sequence. Regulatory elements include, for example, promoters, cis-regulatory elements, enhancers, introns or terminators. Depending on the type of regulatory element it is located on the nucleic acid molecule before (i.e., 5' of) or after (i.e., 3' of) the protein-encoding nucleotide sequence. The regulatory elements are functional in a living plant cell.

The term "operatively linked" means that a regulatory element is linked in such a way with the protein-encoding nucleotide sequence, i.e. is positioned in such a way relative to the protein-encoding nucleotide sequence on, for example, a nucleic acid molecule that an expression of the protein-encoding nucleotide sequence under the control of the regulatory element can take place in a living cell.

For the purposes of the present invention, a "promoter" is a nucleotide sequence regulating the expression of a gene, which typically is located at the 5' end of a gene and mediates the start of transcription by RNA polymerase by interaction with certain DNA-binding proteins. Examples of promoters which are functional in plant cells, include constitutive promoters such as viral promoters, for example, the CaM35S promoter, a double CaM35S promoter, or plant promoters such as the ubiquitin promoters as described in EP 0 305 668 and U.S. Pat. No. 6,528,701. Furthermore, promoters may be used, which have, for example, specific activity at certain stages of development or which are inducible by environmental factors such as biotic or abiotic stress, or which are tissue-specific. Especially those promoters can be used, which show increased specificity for the saccharose storage organ or parts thereof, i.e., which are active in particular in this saccharose storage organ or parts thereof. For sugar beet, the promoter may be, for example, a root-specific or taproot-specific promoter. The person skilled in the art knows them from the prior art: WO 02/40687, Oltmanns, H. et al. (2006) "Taproot promoters cause tissue specific gene expression within the storage root of sugar beet", *Planta* 224: 485-495, Noh, Seol Ah, et al. (2012) "A sweetpotato SRD1 promoter confers strong root, taproot-, and tuber-specific expression in *Arabidopsis*, carrot, and potato" *Transgenic research* 21: 265-278. For sugarcane preferably culm-specific promoters may be used, such as those known from Goshu Abraha, Tsion. "Isolation and characterization of a culm-specific promoter element from sugarcane", diss. Stellenbosch: University of Stellenbosch, 2005. Govender, C. "Stem specific promoters from *sorghum* and maize for use in sugarcane", diss. Stellenbosch: Stellenbosch University, 2008; and Mudge, S. R. et al. (2013) "Mature-stem expression of a silencing-resistant sucrose isomerase gene drives isomaltulose accumulation to high levels in sugarcane," *Plant Biotechnology Journal* 1: 502-509).

Furthermore, suitable promoters include synthetic promoters. These are promotors that have been created by molecular biology techniques that are not found in nature in this configuration. A synthetic promoter is a minimalistic promoter containing only one or more selected, defined cis-elements in addition to a minimal promoter. These cis-elements are binding sites for DNA-binding proteins such as transcription factors and are isolated from natural promoters, derived from previously isolated cis-elements, or produced technically by random recombination techniques and selected by appropriate methods; as compared with a natural promoter, due to its less complex construction a synthetic promoter is activated only by a few exogenous and endogenous factors and is therefore more specifically regulated.

The "minimal promoter" or "core"-promoter is a nucleotide sequence which contains the binding sites for the basal transcription factor complex and allows the accurate initiation of transcription by RNA polymerase II. Characteristic sequence motifs of the minimal promoter are the TATA box, the initiator element (lnr), the "TFBII recognition element" (BRE) and the "downstream core promoter element" (OPE). In the minimal promoter these elements can occur individually or in combination. The minimal promoter is or its sequence motifs are available, for example, from any plant, bacterial, fungal or viral gene.

"Cis elements" are nucleotide sequences that are located on the same nucleic acid molecule as the protein-encoding nucleotide sequence to be expressed. Cis elements do not have to encode RNA or protein and in the direction of transcription can be located before or after the protein-encoding nucleotide sequence to be expressed. Cis elements upstream before a protein-encoding nucleotide sequence to be expressed often provide necessary binding motifs in particular for transcription factors which engage as trans-acting elements (of Lat. trans, 'beyond'), on the molecular level, from the other side in the regulation of the transcription of this gene. If, in addition, cis elements lead to an inhibition of the transcription, they are called silencers. Cis elements that lead to an enhancement of the transcription are called enhancers. The totality of the cis/trans activities in the promoter determines the intensity with which the RNA polymerase carries out transcription.

Furthermore, a promoter may be a chimeric promoter and/or a promoter that has been modified by cis elements. The modification of a promoter can also mean the additional incorporation of a cis element in the promoter which for example already has a cis-element naturally. Further, the modification also includes a multimerization of a cis element, in particular a multimerization of a naturally existing cis element. Compared with the native version such modified promoter may have altered properties with respect to specificity, expression level or background activity, for example.

Terminators are nucleotide sequences on the DNA, which usually mark the end of a gene and lead to the termination of transcription.

According to an alternative and/or additional embodiment, the nucleotide sequence encoding the tonoplast proton/sugar antiporter protein, particularly the nucleotide sequence encoding the tonoplast proton/saccharose antiporter protein, and the nucleotide sequence of the at least one regulatory element are heterologous. This means that they are derived from different species or do not occur naturally in a species in the intended combination.

According to a third aspect, the invention relates to a vector or mobile genetic element, comprising a nucleic acid molecule having a nucleotide sequence according to the first aspect or a recombinant gene according to the second aspect.

Here, a vector means a transport vehicle for a nucleic acid molecule according to the first aspect or a recombinant gene according to the second aspect, in particular for the transfer of a foreign nucleic acid into a living recipient cell. The living recipient cell may be a eukaryotic cell or a prokaryotic cell. The vectors include, for example, plasmids, cosmids, yeast artificial chromosomes (YACs), bacterial artificial chromosomes (BACs) or P1 artificial chromosomes (PACs) as well as modified viruses such as adenoviruses, retroviruses and phages.

Mobile genetic elements are nucleotide sequences, the position of which in the genome of an organism is variable. The mobile genetic elements include, for example, self-serving nucleotide sequences such as transposons, retro elements, insertion sequences and inteins, but also group II introns, inserting plasmids and certain bacteriophages such as the Mu phage.

According to a further aspect, the invention relates to a eukaryotic host cell or a prokaryotic host cell comprising a nucleic acid molecule according to the first aspect as a transgene, a recombinant gene according to the second aspect as a transgene or a vector or mobile genetic element according to the third aspect as a transgene. This means that the nucleic acid molecule, the recombinant gene and/or the vector or mobile genetic element has been incorporated into the host cell, for example by means of transformation or transfection. Examples of prokaryotic host cells are bacteria of the genus *A. tumefaciens, E. coli* and *B. subtilis*. Examples of eukaryotic host cells are yeast cells such as *Saccharomyces* or *Schizosaccharomyces*, but also cells of animal or plant origin.

According to a further aspect, the invention relates to proteins which function as tonoplast proton/saccharose antiporter. This antiporter is specific for saccharose. Preferably, the protein is encoded by a nucleic acid molecule according to the first aspect.

According to an embodiment, the tonoplast proton/saccharose antiporter protein is selected from the group of proteins which
a) have an amino acid sequence according to SEQ ID NO: 1;
b) have an amino acid sequence which has an identity of at least 80% to the amino acid sequence according to SEQ ID NO: 1;
c) are a homolog, an analog or an ortholog of the protein according to SEQ ID NO: 1.

The tonoplast proton/sugar antiporter protein according to SEQ ID NO: 1, also referred to as BvTST2.1, has an amino acid sequence having a length of 735 amino acids. A hydrophobicity analysis indicates that BvTST2.1 apparently has 12 hydrophobic transmembrane domains and a large, centrally located hydrophilic loop that connects the sixth and seventh transmembrane domain. BvTST2.1 has the highest sequence identity to the tonoplast monosaccharide transporter protein 2 from *Arabidopsis thaliana* (AtTMT2). The identity of these two amino acid sequences is 68% and considering conservative and semi-conservative amino acid substitutions they have a sequence similarity of 84% (FIG. 1).

According to a further aspect, the invention relates to proteins which function as tonoplast proton/sugar antiporter. Preferably, the protein is encoded by a nucleic acid molecule according to the first aspect.

According to an embodiment, the tonoplast proton/sugar antiporter protein is selected from the group of proteins which
a) have an amino acid sequence according to SEQ ID NO: 3, 5 or 7;
b) have an amino acid sequence which has an identity of at least 80% to the amino acid sequence of SEQ ID NO: 3, 5 or 7;
c) are a homolog, an analog or an ortholog of the protein according to SEQ ID NO: 3, 5 or 7.

The tonoplast proton/sugar antiporter protein according to SEQ ID NO: 3 is also referred to as BvTST1, according to SEQ ID NO: 5 is also referred to as BvTST2.2 and according to SEQ ID NO: 7 is also referred to as BvTST3

Since the tonoplast proton/saccharose antiporter protein BvTST2.1 identified in *Beta vulgaris* as well as the other tonoplast proton/sugar antiporter proteins BvTST1, BvTST2.2 and BvTST3 also has/have sequence identities to transport proteins from other plants, the tonoplast proton/sugar antiporter proteins, in particular the tonoplast proton/saccharose antiporter proteins also comprise proteins whose amino acid sequence has an identity of at least 80% to the amino acid sequence of SEQ ID NO: 1, 3, 5 or 7, preferably of at least 85%, at least 90%, at least 95%, at least 96%, at least 97%, at least 98% or at least 99%, as well as homologs, analogs or orthologs thereof. In this context it is irrelevant in which species these proteins occur naturally or whether these are not naturally occurring proteins that are produced for example by means of molecular genetic methods.

According to a further aspect, the invention relates to a transgenic plant cell comprising a nucleic acid molecule according to the first aspect as a transgene, a recombinant gene according to the second aspect as a transgene or a vector or mobile genetic element according to the third aspect as a transgene, as well as a transgenic plant or parts thereof comprising at least one such plant cell. In this context, the transgenic plant or parts thereof also comprise(s) a nucleic acid molecule according to the first aspect as a transgene, a recombinant gene according to the second aspect as a transgene or a vector or mobile genetic element according to the third aspect as a transgene.

According to a further aspect, the invention relates to seeds of a transgenic plant according to the preceding aspect, wherein the seeds and in particular at least an embryonic cell of the seeds comprises a nucleic acid molecule according to the first aspect as a transgene, a recombinant gene according to the second aspect as a transgene or a vector or mobile genetic element according to the third aspect.

In an embodiment, the plant cell is the cell of a monocotyledonous plant. In another embodiment, the plant cell is a cell of a dicotyledonous plant. According to another and/or additional embodiment, the plant cell is cells of a plant, which is selected from the group of species or parent genera comprising *Beta vulgaris, Saccharum officinarum, Arenga saccharifera, Acer saccharum* and *Sorghum* sp. Accordingly, according to another embodiment, the transgenic plant is selected from the group comprising *Beta vulgaris, Saccharum officinarum, Arenga saccharifera, Acer saccharum* and *Sorghum* sp. According to another embodiment, the parts of a transgenic plant or the seeds of a transgenic plant are derived from the group of plants comprising *Beta vulgaris, Saccharum officinarum, Arenga saccharifera, Acer saccharum* and *Sorghum* sp.

In an additional and/or alternative embodiment, the transgenic plant cell, the transgenic plant or the parts of the transgenic plant, which preferably are the saccharose storage organ of the plant, have a higher saccharose concentration than the isogenic plant cell or plant cultured under identical conditions. Further, parts of a plant can be connected to the entire intact plant or be separated therefrom. Such parts include, for example, organs, tissues, cells, and seeds of the plant.

Preferably, the higher saccharose concentration is based on a higher saccharose concentration in the plant vacuole, in particular in the vacuole of at least one cell of the saccharose storage organ of the plant. Particularly preferably, a plant with a higher saccharose concentration also has an increased saccharose yield. In this context, yield means the yield of saccharose from the saccharose storage organ with respect to a defined area under cultivation (e.g., a hectare) or with respect to the weight of a saccharose storage organ taking into account the water content in the saccharose storage organ (preferably normalization is done with respect to fresh weight or dry weight).

According to a further aspect, the invention relates to a method for producing transgenic plants, wherein said method comprises at least the following steps:
(a) incorporating a nucleic acid molecule according to the first aspect, a recombinant gene according to second aspect, and/or a vector or mobile genetic element according to the third aspect in at least one cell of a plant, and
(b) regenerating said transgenic plant from the plant cell obtained in step a).

According to an embodiment, the transgenic plant resulting from the method is capable of concentrating saccharose in the vacuoles of its cells, preferably in the vacuoles of the cells of its saccharose storage organ to a higher level than an isogenic control plant cultured under identical conditions.

For the purposes of the present invention "isogenic plants or control plants" or "isogenic plant cells" mean those plants or plant cells, which were used as starting material for the generation of the transgenic plants or transgenic plant cells. Thus, the genome of the transgenic plants and/or plant cells, to the extent that these are genetically modified plants or plant cells, is/are not different, except for the genes transferred by gene technology and/or incorporated nucleotide sequences.

According to an additional and/or alternative embodiment, the transgenic plant expresses or overexpresses the nucleotide sequence encoding at least one proton/sugar antiporter protein in at least one cell.

Incorporating the nucleic acid molecule, for example by way of transformation, may be accomplished with techniques that are basically known to the person skilled in the art. For example, the nucleic acid molecule can be incorporated into the plant cells by infecting a plant tissue or a plant cell with *Agrobacterium tumefaciens* containing the nucleic acid sequence to be transferred in its plasmid that can be integrated into the plant genome. Incorporating by means of a biolistic transfer is another option, wherein the nucleic acid to be incorporated into the plant cell is applied to gold particles or tungsten particles, which are then shot into the cells at a high speed. Another option known to the person skilled in the art for incorporating the nucleic acid into a plant cell, is the protoplast transformation, wherein either polyethylene glycol is added to the protoplasts in the presence of the nucleic acid molecules to be incorporated, or the protoplasts are exposed to a short current impulse, so that the protoplast membrane transiently becomes permeable for the nucleic acid molecules. Methods for regenerating whole plants from transformed tissue or cells are also known to the person skilled in the art from the prior art.

Preferably, the nucleic acid molecule according to the first aspect, the recombinant gene according to the second aspect and/or the vector or mobile genetic element according to the third aspect are stably incorporated into the genome of the cell of the plant. This means following regeneration of a plant the transferred nucleic acid sequence may be stably passed from this plant to a progeny plant.

Preferably, the transformation and regeneration of sugar beet is carried out by the method described by Lindsey (Lindsey K. (1991) "Regeneration and transformation of sugar beet by *Agrobacterium tumefaciens*" Plant Tissue Culture Manual B7: 1-13, Kluwer Academic Publishers).

The transgenesis of the plants can be verified by polymerase chain reaction using appropriate oligonucleotide primers. After regeneration, the transformants can be grown and selfed for obtaining seeds in the greenhouse.

In an embodiment, the plant cells to be transformed are cells of monocotyledonous plants. In another embodiment, the plant cells to be transformed are cells of dicotyledonous plants. According to another and/or additional embodiment, the plant cells to be transformed are cells of a plant that is selected from the group of species or the parent genera comprising *Beta vulgaris, Saccharum officinarum, Arenga saccharifera, Acer saccharum* and *Sorghum* sp.

According to another aspect, the invention relates to methods for increasing the saccharose concentration of a saccharose storage organ of a plant by expression or overexpression of a tonoplast proton/sugar antiporter protein, in particular a tonoplast proton/saccharose antiporter protein, in at least one cell of the plant. The expression or overexpression may be obtained by genetic modification of at least one cell of the plant, and comprises
(1) incorporating a nucleic acid molecule according to the first aspect, a recombinant gene according to the second aspect and/or a vector or mobile genetic element according to the third aspect, in at least one cell of a plant, thereby causing an additional expression or overexpression of a tonoplast proton/sugar antiporter protein, or
(2) genetically modifying an endogenous regulatory element, such as a promoter, which regulates the expression of an endogenous gene encoding a tonoplast proton/sugar antiporter protein, for example by inserting additional cis elements or enhancers, thereby causing an increased expression of the regulated tonoplast proton/sugar antiporter protein.

By expression or overexpression of a tonoplast proton/sugar antiporter protein, in particular a tonoplast proton/saccharose antiporter protein, in at least one cell of the plant, the import of saccharose in the vacuoles of the genetically modified cell is improved. This also increases the saccharose concentration in the vacuoles of this cell compared to an isogenic plant cell.

An "increase in saccharose concentration" or an "increased saccharose concentration" or a "higher saccharose concentration of a saccharose storage organ of a plant" means an increase in the average saccharose concentration, based on the fresh weight of the saccharose storage organ, as compared with a non-transgenic (isogenic) control plant cultured under identical conditions of at least 0.2%, 0.4%, 0.6%, 0.8% or 1%, preferably of at least 1.2%, 1.4%, 1.6%, 1.8% or 2%, particularly preferably of at least 2.5%, 3%, 3.5%, 4%, 4.5%, 5%, 6%, 7%, 8%, or 10%, and most preferably of at least 15%.

For the purposes of the invention the term "overexpressed" means that the amount of tonoplast proton/sugar antiporter protein in a plant, plant cell or tonoplasts thereof is higher than in the isogenic plant, isogenic plant cell or the tonoplasts thereof.

According to an embodiment, the method for increasing the saccharose concentration of a saccharose storage organ of a plant comprises the expression and/or overexpression of the nucleotide sequence of a nucleic acid molecule encoding a tonoplast proton/sugar antiporter protein according to the first aspect of the invention.

For this purpose, a transgenic plant is produced according to the method described above, wherein the expression and/or overexpression of the proton/sugar antiporter protein(s) in the transgenic plant as described above can be facilitated by various genetic modifications.

For example, a construct consisting of a strong promoter and a nucleotide sequence according to the first aspect of the invention can be incorporated into a plant cell to be transformed. Alternatively, the endogenous promoter of a gene encoding a tonoplast proton/sugar antiporter protein, in particular a gene encoding a tonoplast proton/saccharose antiporter protein, may be modified in such a way that it is more active in the transgenic plant than in the isogenic control plant. Means for modifying an endogenous promoter can be, for example, TALENs or zinc finger nucleases. According to another alternative, additional gene copies of the endogenous gene encoding a tonoplast proton/sugar antiporter protein, in particular the endogenous gene encoding a tonoplast proton/saccharose antiporter protein, including its natural promoter, can be incorporated into the plant cell.

In an alternative and/or additional embodiment, the tonoplast proton/saccharose antiporter protein is selected from the group comprising BvTST2.1 proteins, homologs, analogs, and orthologs thereof.

In another aspect, the invention relates to methods for identifying a plant that is suitable to generate an increased saccharose concentration in its saccharose storage organ.

According to an embodiment, the plants to be identified may be subjected to marker-assisted identification. For this purpose, the DNA of each plant to be examined is isolated and either subjected to polymerase chain reaction (PCR) using appropriate oligonucleotide primers, so that those plants can be identified which, due to their genetic makeup, are suitable to generate an increased saccharose concentration in their saccharose storage from the analysis of the reaction products of the PCR, either by gel chromatography or by means of fluorescence detection as in RT-PCR.

According to an additional and/or alternative embodiment the genetic makeup of the plant to be identified can be carried out by means of a restriction length polymorphism, wherein the isolated DNA is hydrolyzed with various restriction endonucleases, the restriction fragments are separated by gel chromatography, blotted and hybridized with an appropriate probe. Suitable exemplary oligonucleotides for an identification of transgenic plants which are suitable of generating an increased saccharose concentration in their saccharose storage organ, because they express or overexpress the nucleotide sequence of SEQ ID NO: 2 may be selected from the group of oligonucleotides comprising SEQ ID NO: 15 to SEQ ID NO: 26. The person skilled in the art knows how to provide suitable oligonucleotides also for homologs, analogs or orthologs of SEQ ID NO: 2.

According to an additional and/or alternative embodiment, the identification of the plants that are suitable to generate an increased saccharose concentration in their saccharose storage organ is not carried out based on their genetic makeup, but by the expression of their tonoplast proton/saccharose antiporter proteins. This can take place, for example, at the level of mRNA by determining the amount of mRNA of the deoxyribonucleotide sequences encoding for the tonoplast proton/sugar antiporter proteins, in particular of the deoxyribonucleotide sequences encoding for the tonoplast proton/saccharose antiporter proteins, for example, by "quantitative real-time PCR". The determination of a larger amount of mRNA encoding at least one tonoplast proton/sugar antiporter protein described above in a plant, a plant tissue or a plant cell, particularly in a tissue or a cell of the saccharose storage organ of the plant, relative to a comparison plant of the same species or a part thereof, or relative to another plant tissue or plant cell of the same plant, which is not part of the saccharose storage organ of the plant, is considered proof of the suitability of a plant to generate an increased saccharose concentration in their saccharose storage organ.

An identification of the plants that are suitable to generate an increased saccharose concentration in their saccharose storage organ, can also take place by the quantitative detection of the amount of tonoplast proton/sugar antiporter protein, in particular of tonoplast proton/saccharose antiporter protein in plant part. For this purpose a so-called Western blot is used, wherein the electrophoretically separated proteins of the plant part, preferably of the vacuoles, particularly preferably of the vacuolar membrane of this part are incubated with an antibody specific for one or more tonoplast proton/sugar antiporter proteins described above. By means of a secondary antibody that binds the antibody specific for one or more tonoplast proton/sugar antiporter proteins described above, and having a detectable label, the amount of tonoplast proton/sugar antiporter protein, in particular tonoplast protons/saccharose antiporter protein, can be determined in the part of the plant and those plants can be identified which are suitable to generate an increased saccharose concentration in their saccharose storage organ. The determination of a larger amount of at least one tonoplast proton/saccharose antiporter protein in a plant, a plant part or a plant cell, particularly in a tissue or a cell of the saccharose storage organ of the plant, relative to a comparative plant of the same species or a part thereof or relative to another plant tissue or plant cell of the same plant, which is not part of the saccharose storage organ of the plant, is considered proof of the suitability of a plant to generate an increased saccharose concentration in their saccharose storage organ.

Thus, the present invention encompasses also the plants identified with the aforementioned method that are suitable to generate an increased saccharose concentration in their saccharose storage organ. According to a further aspect, the invention relates to oligonucleotides which are suitable for use as molecular markers for the diagnostic detection of a nucleic acid molecule according to the first aspect.

According to an embodiment, at least one of the suitable oligonucleotides is selected from the group comprising the oligonucleotides according to SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26. They can be used as molecular markers for the diagnostic detection of a nucleic acid molecule having a nucleotide sequence of SEQ ID NO: 2.

According to another aspect, the invention relates to antibodies which are diagnostic of a protein that functions as tonoplast proton/sugar antiporter, preferably as tonoplast proton/saccharose antiporter.

In an embodiment, the diagnostic antibody is a monoclonal antibody. In an alternative embodiment, the diagnostic antibody is part of a polyclonal antiserum.

In an additional and/or alternative embodiment, the diagnostic antibody or the polyclonal antiserum specific for a particular tonoplast proton/sugar antiporter protein such as a tonoplast proton/saccharose antiporter protein. Preferably the diagnostic antibody recognizes and binds an epitope on the loop between the sixth and seventh transmembrane domain of a proton/saccharose antiporter protein According to a further aspect, the invention relates to the use of a tonoplast proton/sugar antiporter protein for increasing the saccharose concentration of a saccharose storage organ of a plant.

According to an embodiment using a tonoplast proton/sugar antiporter protein for increasing the saccharose concentration of a saccharose storage organ of a plant comprises increasing the saccharose concentration by expression or overexpression of a nucleic acid molecule encoding the tonoplast proton/sugar antiporter protein. Preferably, the nucleic acid molecule comprises
i. a nucleic acid molecule having a nucleotide sequence according to SEQ ID NO. 2, 4, 6, 8, 10, 12 or 14, or having a nucleotide sequence having an identity of at least 80% to one of the nucleotide sequences according to SEQ ID NO: 2, 4, 6, 8, 10, 12 or 14;
ii. a nucleic acid molecule having a nucleotide sequence that is complementary to one of the nucleotide sequences according to i.;
iii. a nucleic acid molecule that hybridizes with one of the nucleic acid molecules according to i. or ii.; or
iv. a nucleic acid molecule encoding a polypeptide having an amino acid sequence according to SEQ ID NO: 1, 3, 5, 7, 9, 11 or 13, or encoding a polypeptide having an amino acid sequence having an identity of at least 80% to one of the amino acid sequences according to SEQ ID NO: 1, 3, 5, 7, 9, 11 or 13.

The nucleic acid molecule according to SEQ ID NO: 2 encodes the tonoplast proton/sugar antiporter TST2.1 from *Beta vulgaris* having the amino acid sequence according to SEQ ID NO: 1.

The nucleic acid molecule according to SEQ ID NO: 4 encodes the tonoplast proton/sugar antiporter TST1 from *Beta vulgaris* having the amino acid sequence according to SEQ ID NO: 3.

The nucleic acid molecule according to SEQ ID NO: 6 encodes the tonoplast proton/sugar antiporter TST2.2 from *Beta vulgaris* having the amino acid sequence of SEQ ID NO: 5.

The nucleic acid molecule according to SEQ ID NO: 8 encodes the tonoplast proton/sugar antiporter TST3 from *Beta vulgaris* having the amino acid sequence according to SEQ ID NO: 7.

The nucleic acid molecule according to SEQ ID NO: 10 encodes the tonoplast proton/sugar antiporter TMT1 of *Arabidopsis thaliana* having the amino acid sequence according to SEQ ID NO: 9.

The nucleic acid molecule according to SEQ ID NO: 12 encodes the tonoplast proton/sugar antiporter TMT2 of *Arabidopsis thaliana* having the amino acid sequence according to SEQ ID NO: 11.

The nucleic acid molecule according to SEQ ID NO: 14 encodes the tonoplast proton/sugar antiporter TMT3 of *Arabidopsis thaliana* having the amino acid sequence according to SEQ ID NO: 13.

By the expression and/or overexpression of at least one of the nucleotide sequences mentioned under i. to iv. in a plant after incorporating it into at least one cell of the plant, the amount of proton/sugar antiporter protein in the vacuole of this plant can be increased, particularly in the membranes of the vacuoles of the saccharose storage organs of this plant, so that more saccharose can be transported into the vacuoles of the plant, and the saccharose concentration in the saccharose storage organ of the plant compared to an isogenic control plant cultured under identical conditions, is increased. This allows to increase the saccharose yield per plant, per saccharose storage organ and/or per acreage.

The present invention will now be illustrated by exemplary embodiments, wherein the exemplary embodiments are for illustrative purposes only, but not limit the present invention. The present invention is defined solely by the claims. The term "a" or "an" is not to be understood as specifying the number.

The exemplary embodiments clearly show that the TST2.1 from *Beta vulgaris* is the tonoplast membrane protein that can import highly specifically saccharose into the vacuole of a plant cell as proton/sugar antiporter.

EXAMPLE 1: PLANT MATERIAL AND GROWTH CONDITIONS

For the following experiments sugar beet varieties "Belladonna KWS" and "Brigadier" were used. The seeds of the variety "*Belladonna* KWS" were provided by KWS Saat AG, Einbeck, DE, the seeds for beet of the variety "Brigadier" were purchased in local seed businesses.

Furthermore, plants and plant cells of *Nicotiana benthamiana* and *Arabidopsis thaliana* were used. The plants grew in growth chambers on the standard substrate ED 73 of the company Einheitserde- and Humuswerke Gebr. Patzer GmbH & Co. KG at a light-dark cycle of 10 hours of light and 14 hours darkness, 22° C. and 125 µmol quanta $m^{-2} s^{-1}$.

The *Arabidopsis* Attst1-2 T-DNA double gene knockout mutant has been described in the prior art (Wormit, A. et al. (2006) "Molecular identification and physiological characterization of a novel monosaccharide transporter from *Arabidopsis* involved in vacuolar sugar transport" Plant Cell 18, 3476-3490). For growth experiments with 2-deoxyglucose surface sterilized *Arabidopsis* seeds were seeded on semi-concentrated Murashige and Skoog (½MS) agar plates as described (Reiser, J. et al. (2004) "Molecular physiological analysis of the two plastidic ATP/ADP transporters from

*Arabidopsis*", Plant Physiol. 136: 3524-3536). The selection of the pUBQ:BvTST2.1-GFP and 35S:BvTST1 overexpressing plants was carried out on ½MS agar plates containing either 50 µg/ml hygromycin or 40 µg/ml kanamycin.

EXAMPLE 2: QUANTITATIVE DETERMINATION OF SUGARS IN TISSUES OF SUGAR BEET

Taproot tissue of sugar beet was harvested with a vegetable slicer, immediately frozen in liquid nitrogen and stored until quantitative glucose testing at −80° C. For the determination of the sugar content, the plant tissue was ground in liquid nitrogen and 50 µg ground tissue was extracted twice for 20 minutes at 80° C. with 80% ethanol. The supernatants were combined and evaporated with a SpeedVac (Eppendorf, Hamburg, Germany). The dried sugars were dissolved in water and quantified by means of a NADP-coupled enzymatic assay in a microplate reader as described (Bergmeyer, H. U. and Bernt, E. (1974) "Methods of Enzymatic Analysis", vol. 3, Bergmeyer, H. U. ed., Verlag Chemie New York, S. 1176-117; Lee, Y. C. (1972) "α-Mannosidase, β-glucosidase, and β-galactosidase from sweet almond emulsion" Methods Enzymol. 28: 699-702).

EXAMPLE 3: GENE EXPRESSION ANALYSIS

The relative accumulation of mRNA was carried out by Northern blot analyses as described (Young, B. et al. (2011) "*Arabidopsis* nucleoside hydrolases involved in intracellular and extracellular degradation of purines" Plant J. 65: 703-711). Quantitative RT-PCR was performed as previously described (Leroch M. et al (2005) "Identification and characterization of a novel plastidic adenine nucleotide uniporter from *Solanum tuberosum*" J. Biol. Chem. 280: 17992-18000). The gene-specific primers that were used are listed in Table 1:

TABLE 1

Gene-specific primers for the amplification of the nucleotide sequences encoding BvTST1 and BvTST2.1, and for the quantitative PCR for expression analysis of the four paralogous TST gene from Beta vulgaris.

| Name | Nucleotide sequence | SEQ ID NO: |
|---|---|---|
| BvTST1 GWfw | GGGGACAAGTTTGTACAAAAAAGCAGGCTTAATGAAGGGTGCTGTGCTT | 15 |
| BvTST1GW rev | GGGGACCACTTTGTACAAGAAAGCTGGGTACTCCGCCTTAGCGGCTTC | 16 |
| BvTST2.1fw_XhoI | CTCGAGATGAGTGCAGCAGTATTAG | 17 |
| BvTST2.1rev_XbaI | TCTAGAGTGGCTTGCTTGTCTTGCACC | 18 |
| qPCRfwTST1 | GCTGTTGCTATGAGGCTCATGGA | 19 |
| qPCRrevTST1 | CCTTAGCGGCTTCTAACTGTTTAGG | 20 |
| qPCRfwTST2.1 | AAAGATGAACACCACTGTGTATG | 21 |
| qPCRrevTST2.1 | GTCATCAGTGGCTTGCTTGTCTTG | 22 |
| qPCRfwTST2.2 | AAAGATGAGCACTACTGTGCACG | 23 |
| qPCRrevTST2.2 | TCAGTTGTCCTTGTCTTCAGAAGG | 24 |
| qPCRfwTST3 | TCTACTTCTGCTGCTTTGTCATGG | 25 |

TABLE 1-continued

Gene-specific primers for the amplification of the nucleotide sequences encoding BvTST1 and BvTST2.1, and for the quantitative PCR for expression analysis of the four paralogous TST gene from Beta vulgaris.

| Name | Nucleotide sequence | SEQ ID NO: |
|---|---|---|
| qPCRrevTST3 | TCAGCTTCAGCTTGCCTTGCA C | 26 |
| Bvef1a_fw | CCACATTGCTGTCAAGTTTGCTG | 27 |
| Bvef1a_rev | TGGTAACCTTGGCACCGGTTG | 28 |

EXAMPLE 4: ISOLATION OF VACUOLES AND TONOPLAST MEMBRANE FROM TAPROOT TISSUE

Vacuoles were isolated by the method of Leigh and Branton (Leigh, R. A. and Branton, D. (1976) "Isolation of Vacuoles from Root Storage Tissue of *Beta vulgaris*" L. Plant Physiol 58: 656-662) with the following changes: taproot tissue was cut into slices of 0.1 to 0.2 mm thickness with a vegetable slicer, and immediately incubated in a collection medium (1 M sorbitol, 1 mM DTT, 5 mM EDTA, 50 mM Tris-HCl, pH 7.6) at room temperature. Subsequently, the thin slices of the taproot tissue were comminuted with a razor blade in the collection medium (1 M sorbitol, 1 mM DTT, 5 mM EDTA, 50 mM Tris-HCl, pH 7.6), filtered through a stainless steel sieve (100 mm mesh size) and sedimented by centrifugation (2,000×g, 20 min, 4° C.). The sediment was resuspended in collection medium with 30% Nycodenz (Axis-Shield GmbH, Heidelberg, Germany) and transferred to 17 ml centrifuge tubes (Beckman UltraClear). In the following swinging bucket centrifugation (1,500×g, 15 min, 8° C.) the Nycodenz forms a density gradient, and the vacuoles floated on the upper phase of the density gradient.

The membranes of vacuoles were isolated as described in the prior art (Schulze W. X. et al. (2012) "Cold acclimation induce changes in *Arabidopsis* tonoplast protein abundance and activity and alters phosphorylation of tonoplast monosaccharide transporters", Plant J. 69: 529-541). The activity of α-mannosidase in sonicated vacuoles was performed as described elsewhere (Boller, T. and Kende, H. (1979) "Hydrolytic enzymes in the central vacuole of plant cells" Plant Physiol 63: 1123-1132; Lee, Y. C. (1972) "α-Mannosidase, β-glucosidase, and β-galactosidase from sweet almond emulsion" Methods Enzymol. 28: 699-702)

EXAMPLE 5: LIQUID CHROMATOGRAPHY AND TANDEM MASS SPECTROMETRY

The sediments of isolated tonoplast membranes of 2 or 5 months old plants were taken up in buffer (4% SDS, 50 mM $NH_4HCO_3$) at a concentration of 1 µg/ml. The proteins taken up were precipitated overnight at −20° C. in 80% acetone and further processed as described by Mühlhaus (Mühlhaus, T. et al. (2011) "Quantitative shotgun proteomics using a uniform 15N-labeled standard to monitor proteome dynamics in time course experiments reveals new insights into the heat stress response of *Chlamydomonas reinhardtii*," Mol.

Cell. Proteomics 10: M110 004739). The extracted peptides were resuspended in 200 µl buffer (2% acetonitrile, 0.4% acetic acid).

Samples of 3 µl of the extracted peptides each were subjected to liquid chromatography-tandem mass spectrometry (LC-MS/MS analysis). The chromatographic separation was carried out on a nanoAquity UPLC (Waters, Eschborn, Germany) by means of a "Symmetry C18 trap column (5 mm particle size, 180 µm×20 mm column dimensions) and a BEH 130 C18 column (1.7 µm particle size, 75 mm×150 mm column dimensions). The eluent was a double gradient, first from 100% Buffer A (0.4% acetic acid, 1% 2-propanol, 2% acetonitrile) to 40% buffer B (0.4% acetic acid, 1% 2-propanol, 90% acetonitrile) within 2 or 3 hours, then to 90% buffer B over 5 min, and finally 15 min with 90% buffer B. The column was equilibrated at the end for 15 min with 100% buffer A. The hybrid LTQ XL-Orbitrap mass spectrometer (ThermoScientific, Hamburg, Germany) was operated in data-dependent mode with a cycle of a complete scan of the mass spectrum 300-1500 m/z (Orbitrap) at a set resolution of 60,000 at 400 m/z, followed by seven successive data-dependent $MS^2$ scans (LTQ) of the most intense ions. Individually charged ions were excluded from the $MS^2$ analysis and the parent ions for $MS^2$ analysis were placed for 20 seconds on an exclusion list. Each sample was analyzed in triplicate.

Proteins were identified using the MaxQuant software and the Andromeda Search Engine (Cox, J. and Mann, M. (2008) "MaxQuant enables high peptide identification rates, individualized p.p.b.-range mass accuracies and proteome-wide protein quantification". Nat. Biotechnol. 26: 1367-72) in a database for sugar beet proteins created in the house of one of the inventors.

EXAMPLE 6: NUCLEIC ACID CONSTRUCTS

Complementary DNA (cDNA) of *Beta vulgaris* was prepared by reverse transcription of RNA isolated from taproots or leaves. All polymerase chain reactions (PCR) were performed with the Phusion HF DNA Polymerase (Thermo Scientific).

The pUBQ:BvTST1-GFP fusion construct was prepared using the vector pUBC-GFP-Dest (Grefen et al (2010) "A ubiquitin-10 promoter-based vector set for fluorescent protein tagging facilitates temporal stability and native protein distribution in transient and stable expression studies", Plant J. 64: 355-365). For this purpose, the cDNA of BvTST1 was amplified and the stop codon was removed by PCR using the BvTST1 primers containing the attB1 and attB2 sites. The amplification product was cloned via a BP reaction in pDONRZEO (Invitrogen, Heidelberg, Germany), followed by an LR reaction in pUBC-GFP-Dest.

The pUBQ:BvTST2.1-GFP construct was prepared as follows: The entire open reading frame of the BvTST2.1 gene was amplified with the primers BvTST2.1fw_XhoI/BvTST2.1rev_XbaI. The resulting PCR product was digested with XhoI and XbaI and ligated into the vector pUBC-cGFP-Dest opened with XhoI and SpeI (Grefen et al. (2010)). The construct so produced contains the bar gene, which in transformed plants results in a Basta resistance. Subsequently, the complete nucleotide sequence encoding BvTST2.1-GFP was excised from this construct using XhoI/PstI, and inserted into a vector pUBN-nYFP-Dest correspondingly opened with XhoI and PstI, which mediates a hygromycin resistance in transformed plants. Digestion of pUBN-nYFP Dest with XhoI/PstI resulted in a complete removal of the nYFP sequence and the "Gateway" properties of the target vector so that it is suitable for the transformation of the Attst1-2 double gene knockout mutants by means of agrobacteria (Clough S. J., Bent, A. F. (1998) "Floral dip: a simplified method for *Agrobacterium*-mediated transformation of *Arabidopsis thaliana*" Plant J. 16: 735-743). The nucleotide sequences of all gene constructs produced were verified by sequence analysis.

EXAMPLE 7: PATCH-CLAMP STUDIES OF VACUOLES OF TRANSFORMED *NICOTIANA BENTHAMINA* PLANTS

For the transient overexpression of sugar transport proteins (BvTST1-GFP and BvTST2.1-GFP) labeled at their C-terminal ends with the green fluorescent protein (GFP) or only with GFP under the control of the ubiquitin promoter (pUBQ10) in mesophyll cells of *N. benthamiana* N. the method described by Latz et al. (2007) of agro-infiltration of 5 to 7-week-old plants (Latz et al. (2007) "In planta AKT2 subunits constitute a pH and Ca2+-sensitive inward rectifying K+ channel" Planta, 225: 1179-1191). Contrary to the method described in the prior art, the *Agrobacterium tumefaciens* strain GV3101 was used as a carrier for nucleotide sequence encoding the gene 19K and for the corresponding sugar transport protein/GFP constructs. The bacteria were cultured overnight in 5 ml YEB medium, centrifuged at 8,000×g for 1 min at room temperature and washed 2 times with Agromix (Latz et al. (2007)). The bacterial cells were resuspended in 3 ml Agromix and kept for 2 to 3 hours at 28° C. in the dark. For infiltration, 1 ml of the suspension with the 19K-containing Agrobacteria was mixed with 1 ml of the suspension of agrobacteria containing pUBQ:BvTST1-GFP, pUBQ:BvTST2.1 GFP or pUBQ:GFP, and 2 ml Agromix were added.

Two days after the agroinfiltration, the protoplasts of the mesophyll cells were isolated essentially as described by Beyhl et al. (Beyhl, D. et al (2009) "The fou2 mutation in the major vacuolar cation channel TPC1 confers tolerance to inhibitory luminal calcium", Plant J. 58: 715-723). After the enzyme incubation of leaf slices for 1 hour, the released protoplasts were washed with 500 mM sorbitol and 1 mM $CaCl_2$. The vacuoles were released directly in the patch clamp chambers from the protoplasts by exposing them to a lysis buffer having an osmolarity of 280 mOsmol×kg$^{-1}$ (10 mM EGTA, 10 mM Hepes/Tris, pH 7.4; osmolarity set with D-sorbitol). Macroscopic currents were measured in the "whole-vacuolar" configuration (Beyhl, D. et al. (2009) "The fou2 mutation in the major vacuolar cation channel TPC1 confers tolerance to inhibitory luminal calcium" *Plant J.* 58: 715-723); and low-pass filtered at 100 Hz. The bath and pipette solution were identical with respect to its composition (100 mM KCl, 2 mM $MgCl_2$, 1 mM $CaCl_2$, 450-500 Osmol×kg$^{-1}$, set with D-sorbitol), except for the pH. The pH of the bath was set to 7.4 (Hepes/Tris) and the pH of the pipette solution was set to 5.5 (Mes/Tris). To measure a sugar induced proton flux, glucose or saccharose was added to the cytoplasmic side of the vacuolar membrane, each in a final concentration of 50 mM.

EXAMPLE 8: ANALYSIS OF THE MEMBRANE PROTEOME OF THE VACUOLES OF CELLS OF THE TAPROOT OF SUGAR BEET

To analyze the proteome of the vacuolar membrane of taproot cells of sugar beet, the vacuoles of the taproot cells of five months old sugar beet (*Beta vulgaris*) of the variety "Belladonna KWS" were isolated and the vacuolar membrane was enriched by high speed centrifugation. The hydrophobic membrane proteins were precipitated with acetone from the several times washed tonoplast fraction, subsequently resuspended in a urea solution (8 M urea) and subjected to tryptic digestion prior to LC-MS/MS analysis.

A total of about 400 different proteins have been identified in each of the enriched tonoplast preparations. One of these proteins, called BvTST2.1 hereinafter (SEQ ID NO: 1), was present in large quantities in all independently carried out preparations, had the signature of a sugar transporter ([LIVMSTAG (SEQ ID NO: 29)]-[LIVMF SAG (SEQ ID NO: 30)]-(SH)-(RDE)-[LIVMSA (SEQ ID NO: 31)]-[DE]-(TD)-[LIVMFYWA (SEQ ID NO: 32)]-G-R-[RK]-x (4.6)-[GSTA (SEQ ID NO: 33)]; prosite pattern PS00216, prosite.expasy.org/) and had the highest similarity to the vacuolar monosaccharide transporter TMT2 from *Arabidopsis thaliana* (FIG. 1).

EXAMPLE 9: GENE FOR TONOPLAST SUGAR TRANSPORT PROTEINS IN THE SUGAR BEET GENOME

When searching the genome of *B. vulgaris* 4 paralogous genes have been identified that encode tonoplast sugar transport proteins. Phylogenetic analysis (FIG. 2) showed that the sugar transporters BvTST1 and BvTST3 are related closest with the orthologous genes AtTMT1 or AtTMT3 of *Arabidopsis*, while BvTST2.1 and BvTST2.2, a very similar pair of genes, have the greatest sequence similarity the *Arabidopsis* ortholog AtTMT2 (FIG. 1). The amino acid sequence of BvTST2.1 corresponds to about 68% to that of AtTMT2 and the similarity is 84% (FIG. 1).

EXAMPLE 10: SUBCELLULAR LOCALIZATION OF BVTST2.1

The subcellular localization of BvTST2.1 was studied in Attst1-2 double gene knockout mutants stably transformed with pUBQ:BvTST2.1-GFP.

The isolation of protoplasts from leaf mesophyll cells and the release of vacuoles was performed by a known method (Yoo, S. D. et al. (2007) "*Arabidopsis* mesophyll protoplasts: a versatile cell system for transient gene expression analysis", Nat. Protocol 1565-1572).

A confocal laser scanning microscope (Leica TCS SP5, Leica Microsystems, Wetzlar, Germany) was used for fluorescence microscopy images. All images were taken with a Leica HCX PL APO 63x/1.20w motCORR CS lens. The image processing was carried out using the Leica Application Suite Advanced Fluorescence Lite software.

After cloning of the complete BvTST2.1 mRNA, the subcellular localization of the protein was determined by stably expressing a BvTST2.1-GFP fusion protein in *Arabidopsis*. The green fluorescence that was observed in mesophyll cells of the leaves of *Arabidopsis* mutants stably expressing BvTS2.1-GFP indicated that the fusion protein was localized in the membrane of the vacuoles, which closely surrounded the chloroplasts.

An enzymatic digest of mesophyll tissue of BvTST2.1-GFP-expressing plants resulted in individual intact protoplasts. The subsequent hypoosmotic treatment of these protoplasts resulted in the release of stable, green fluorescent vacuoles, whereby the localization of BvTST2.1 GFP in the tonoplast was confirmed.

EXAMPLE 11: CORRELATION OF BVTST2.1 EXPRESSION AND SACCHAROSE CONCENTRATION IN TAPROOTS OF SUGAR BEET

To find out about a possible correlation between the expression of BvTST2.1 in the taproots of sugar beet and the saccharose concentration of sugar beet, the expression of the BvTST2.1 gene was determined in the sugar beet varieties "*Belladonna* KWS" and "Brigadier".

Figure 3:
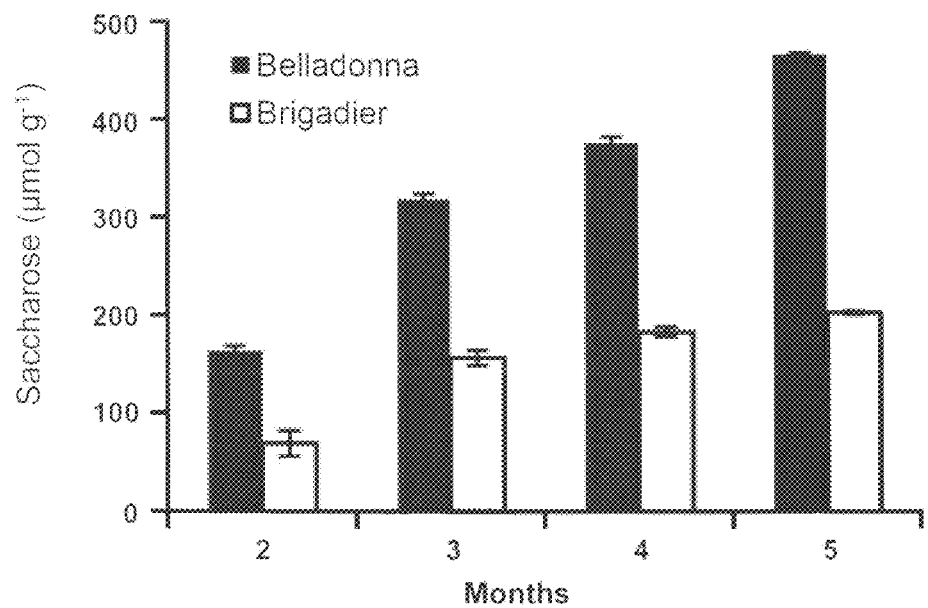
FIG. 3 shows a bar graph illustrating the saccharose concentration taproots of two sugar beet varieties of different age.

The variety "*Belladonna* KWS" is known as a sugar beet variety, which has a high saccharose concentration and as early as two months after planting has a saccharose concentration of about 160 $\mu mol \times g^{-1}$ fresh weight in the taproots (FIG. 3). This high saccharose concentration increased during the following three months of development, reaching about 450 $\mu mol \times g^{-1}$ fresh weight. This corresponds to a 3 fold increase, based on the two-month old taproots.

In contrast, the taproots of the variety "Brigadier" contained less than 70 $\mu mol$ saccharose per fresh weight after two months of growth, and they accumulated only about 195 $\mu mol$ of saccharose per g fresh weight in the next three months (FIG. 3).

When comparing the saccharose concentration of leaves and taproots an approximately 30-fold higher saccharose content was found in the taproots compared with the leaves, while the glucose concentration in the leaves was about 80-fold higher than in the taproots.

Figure 4:
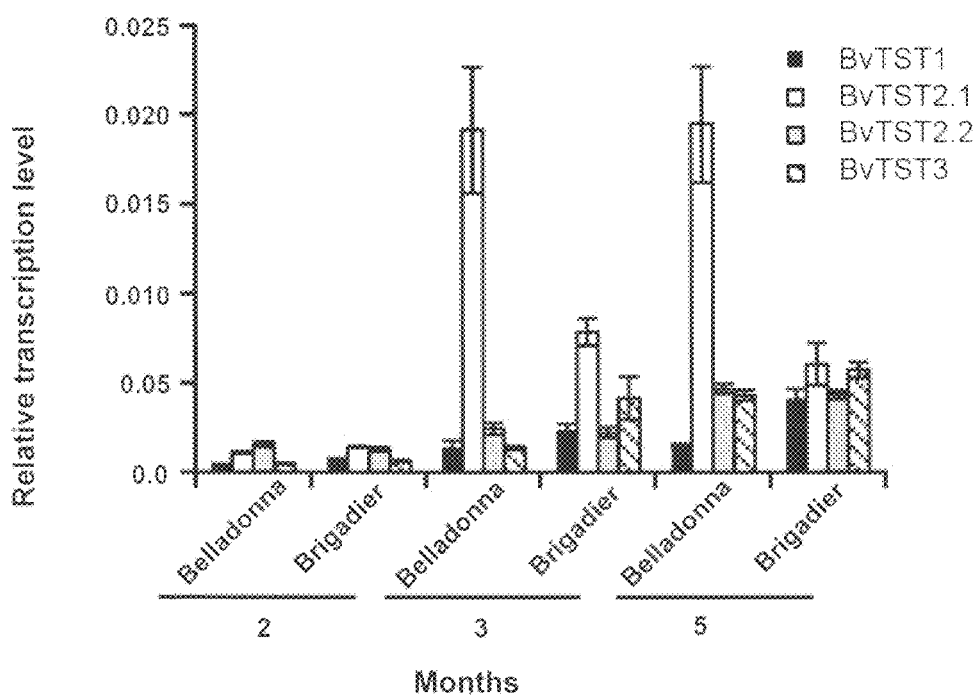
FIG. 4 shows a bar graph indicating the relative amounts of mRNA of the four paralogous TST genes of *Beta vulgaris* in two different sugar beet varieties at different times of development.

The differences in saccharose accumulation between the different sugar beet varieties were also reflected in the amount of mRNA encoding BvTST2.1 (FIG. 4). Both in the taproots of the variety "*Belladonna* KWS" and in the variety "Brigadier" the amounts of mRNA for all four paralogous sugar transporters were low after two months of growth.

After another month of growth and development, the amount of mRNA of BvTST2.1 in both varieties was significantly higher than the amounts of mRNAs encoding BvTST1, BvTST2.2 and BvTST3. In addition, the amount of BvTST2.1 mRNA in the taproots of the variety "*Belladonna* KWS" was about 2.6-fold higher than in the taproots of the variety "Brigadier" (FIG. 4).

While another two months of growth, the amount of BvTST2.1 mRNA in two varieties did not significantly change, compared to the amount after 3 months of growth, so that even after a five-month growth and development phase the amount of mRNA for BvTST2.1 in taproots of the variety "*Belladonna* KWS" was still about 2.6-fold higher than in the taproots of the variety "Brigadier".

Figure 5:
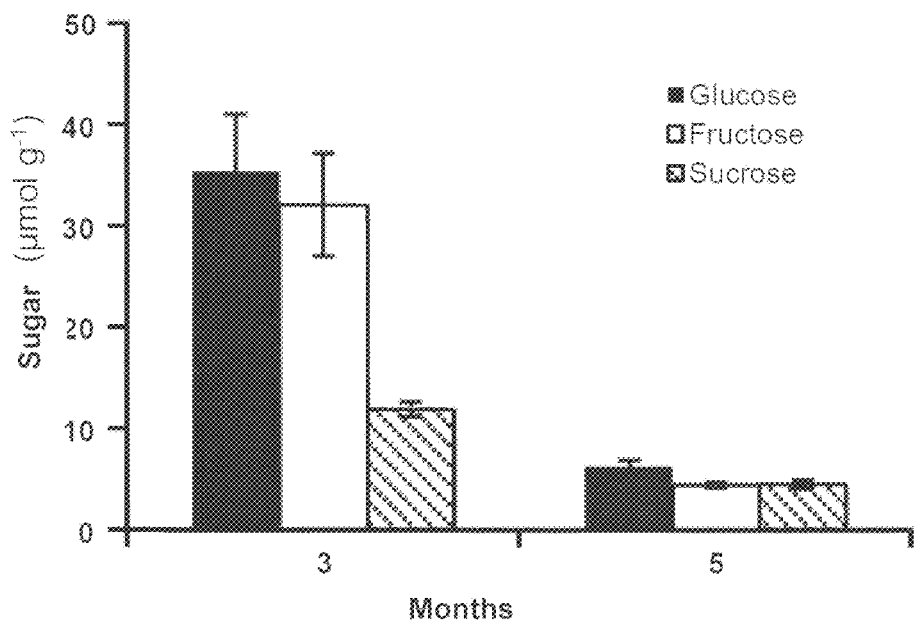
FIG. 5 shows a bar graph illustrating the concentration of various sugars in the leaves of sugar beet variety "*Belladonna* KWS" at different times of development.
Figure 6:
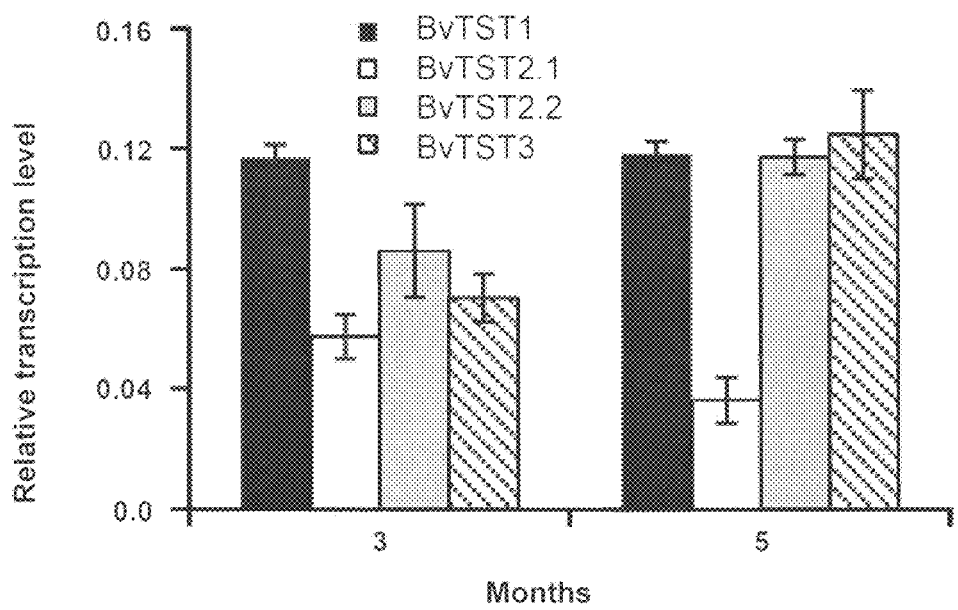
FIG. 6 shows a bar graph indicating the relative amounts of mRNA for the four paralogous BvTST genes in leaves of the sugar beet variety "*Belladonna* KWS" at different times of development.

To gather more information concerning the importance of the BvTST2.1 protein for saccharose storage, the concentrations of glucose, fructose and saccharose were determined in leaves of three- and five-months old sugar beet of the variety "*Belladonna* KWS" (FIG. 5) and compared with the amounts of mRNA of the four TST-paralogs (FIG. 6). In contrast to the taproots, where the glucose and the fructose content was very low, these two monosaccharides accumulated in the leaves. In the leaves of three months old sugar beet, the concentration of glucose and fructose was between 33 and 35 $\mu mol/g$ fresh weight, while the concentration of saccharose was less than 15 $\mu mol/g$ fresh weight. After five months of growth, the concentration of each of the three sugars was between 6 and 9 $\mu mol/g$ fresh weight (FIG. 5).

It was noteworthy that the amount of mRNA for BvTST2.1 in the leaves was consistently lower than the amount of mRNA for BvTST1, BvTST2.2 and BvTST3 while the amount of mRNA for BvTST2.1 in the taproot was always higher than the amount of mRNA for the other isoforms (FIG. 6).

EXAMPLE 12: BVTST2.1 MEDIATED TONOPLAST TRANSPORT OF SACCHAROSE

In order to demonstrate the transport function of BvTST2.1, the "patch clamp" technology has been applied to isolated vacuoles. For this purpose, a BvTST2.1-GFP fusion protein was transiently expressed in mesophyll cells of *Nicotiana benthaminana*. Intact vacuoles of transformed protoplasts were identified by their green color after mild hypo-osmotic lysis.

In order to replicate the physiological proton gradient across the tonoplast of isolated vacuoles, the medium in the pipette, which represents the luminal contents of the vacuole, was buffered to a pH of 5.5, while the medium in the chamber (=Bad), which represents the cytsol, was adjusted to pH 7.5. When saccharose was added to the "cytosolic" medium, the vacuoles reacted with a strong downward deflection of the flow of current. The addition of saccharose in the medium surrounding the isolated vacuoles resulted in an inward current, which suggests a proton antiport of saccharose transport.

Figure 7:
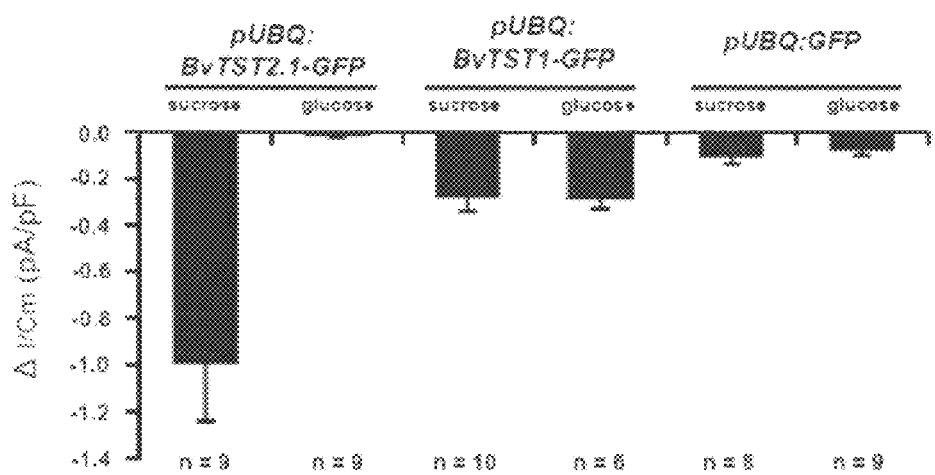
FIG. 7 is a bar graph illustrating the change of the current density induced by the different sugars (saccharides) in vacuoles of transiently transformed mesophyll cells.

In the absence of BvTST2.1, the isolated vacuoles of N benthaminana showed no significant saccharose/proton transport activity. In contrast, in the case of BvTST2.1 containing vacuoles, the addition of saccharose to the chamber medium resulted in an inward flow of current in a magnitude of almost −1 pA/pF (FIG. 7). These currents represent the biological fingerprint of a proton-driven saccharose import across the BvTST2.1-GFP containing vacuolar membrane and is a clear sign that BvTST2.1 couples the export of protons along the proton gradient across the membrane with an import of saccharose against the existing saccharose gradient. The latter function is a biochemical prerequisite for the sugar beet to be able to accumulate high amounts of saccharose in the vacuoles of their taproots.

It is noteworthy that BvTST2.1 does not facilitate any glucose-mediated export of protons. Unlike BvTST2.1, isoform BvTST1 mediates both a saccharose-related and a glucose-related flow of current in the order of about −03, pA/pF (FIG. 7; Table 2).

TABLE 2

Sugar-induced changes in the current density of individual vacuoles. These data demonstrate the specificity of BvTST2.1 for saccharose.

| | Current density [Δ I/Cm (pA/pF)] | | Net ratio |
|---|---|---|---|
| | Saccharose | Glucose | sac/glc |
| BvTST1-GFP | −0.28 ± 0.06 | −0.29 ± 0.04 | 0.81 |
| BvTST2.1-GFP | −1.03 ± 0.29 | −0.018 ± 0.005 | ∞ |
| GFP (control) | −0.11 ± 0.04 | −0.08 ± 0.03 | |

EXAMPLE 13: SACCHAROSE SPECIFICITY OF BVTST2.1 IN VIVO

To analyze the high substrate specificity of BvTST2.1 in living plant cells, AtTMT double gene knockout mutants having none of the two important tonoplast monosaccharide transporter proteins, were transformed with either a PUBQ:BvTST2.1-GFP construct or a pUBQ:BvTST1 construct. The transformants grew in the presence of the toxic glucose analog 2-deoxyglucose. In control experiments without 2-deoxyglucose all plant lines showed a similar growth. In the presence of 2-deoxyglucose the tst1-2 double gene knockout mutants did not develop properly, while wild-type plants and the lines expressing BvTST1 showed a much better growth. The wild-type plants and the BvTST1 expressing double gene knockout mutant grew better in the presence of 2-deoxyglucose probably because 2-deoxyglucose could be transported in the vacuoles for detoxification. The double gene knockout mutant is not able to do so. Those double gene knockout plants expressing BvTST2.1 were unable to compensate the growth arrest of the Attst1-2 double gene knockout mutant in the presence of 2-deoxyglucose, although the BvTST2.1-GFP fusion protein was present in the vacuolor membranes.

The remarkable sensitivity of the Attst1-2::BvTST2.1-GFP plants to 2-deoxyglucose in vivo is consistent with the electrophysiological data and the saccharose specificity of BvTST2.1, which has been obtained by the isolated vacuoles.

The invention claimed is:

1. A method for identifying and cultivating a transgenic and/or genetically modified plant, transgenic and/or genetically modified plant part or seeds of the transgenic and/or genetically modified plant wherein the transgenic and/or genetically modified plant is suitable to generate an increased sucrose concentration in a sucrose storage organ, the method comprising:
   a) isolating mRNA or DNA from the transgenic and/or genetically modified plant, wherein the transgenic and/or genetically modified plant comprises a sucrose storage organ and is at least three months old;
   b) detecting the amount of a nucleic acid molecule in the isolated mRNA or DNA;
   c) identifying the transgenic and/or genetically modified plant in which the amount of the nucleic acid molecule is higher as compared to a reference plant of the same species or a part thereof cultivated under identical conditions; and
   d) cultivating the identified transgenic and/or genetically modified plant, transgenic plant part or seeds of the transgenic and/or genetically modified plant,
   wherein the transgenic and/or genetically modified plant is Beta vulgaris,
   wherein the nucleic acid molecule encodes a tonoplast proton/sugar antiporter specific for sucrose, wherein the nucleic acid molecule comprises:
      a) the nucleotide sequence of SEQ ID NO: 2 or a nucleotide sequence which is at least 90% identical to SEQ ID NO: 2;
      b) a nucleic acid molecule comprising a nucleotide sequence which is complementary to one of the nucleotide sequences according to a); or
      c) a nucleotide sequence encoding a polypeptide comprising the amino acid sequence of SEQ ID NO: 1 or an amino acid sequence which is at least 90% identical to SEQ ID NO: 1, and
   wherein the nucleic acid molecule further comprises at least one heterologous regulatory element.

2. The method of claim 1, wherein the detecting step is conducted by at least one of PCR, RT-PCR, quantitative real-time PCR, or restriction length polymorphism.

3. A method for identifying and cultivating a transgenic and/or genetically modified plant, transgenic and/or genetically modified plant part or seeds of the transgenic and/or genetically modified plant wherein the transgenic and/or genetically modified plant is suitable to generate an increased sucrose concentration in a sucrose storage organ, the method comprising:
   a) isolating mRNA or DNA from at least one taproot of the transgenic and/or genetically modified plant, wherein the transgenic and/or genetically modified plant comprises a sucrose storage organ and is at least three months old;
   b) detecting the amount of a nucleic acid molecule and the amount of mRNA or DNA for BvTST1, BvTST2.2 and BvTST3 in the isolated mRNA or DNA of the at least one taproot;
   c) identifying the transgenic and/or genetically modified plant in which the amount of the mRNA or DNA for the nucleic acid molecule in the at least one taproot is higher than the amount of mRNA or DNA for BvTST1, BvTST2.2 and BvTST3; and
   d) cultivating the identified transgenic and/or genetically modified plant, transgenic and/or genetically modified plant part or seeds of the transgenic and/or genetically modified plant,
   wherein the transgenic and/or genetically modified plant is Beta vulgaris,
   wherein the nucleic acid molecule encodes a tonoplast proton/sugar antiporter specific for sucrose, wherein the nucleic acid molecule comprises:
      a) the nucleotide sequence of SEQ ID NO: 2 or a nucleotide sequence which is at least 90% identical to SEQ ID NO: 2;
      b) a nucleic acid molecule comprising a nucleotide sequence which is complementary to one of the nucleotide sequences according to a); or
      c) a nucleotide sequence encoding a polypeptide comprising the amino acid sequence of SEQ ID NO: 1 or an amino acid sequence which is at least 90% identical to SEQ ID NO: 1, and
   wherein the nucleic acid molecule further comprises at least one heterologous regulatory element.

4. A method for identifying and cultivating a transgenic and/or genetically modified plant, transgenic and/or genetically modified plant part or seeds of the transgenic and/or genetically modified plant wherein the transgenic and/or genetically modified plant is suitable to generate an increased sucrose concentration in a sucrose storage organ, the method comprising:
   a) isolating mRNA or DNA from at least one leaf and at least one taproot of the transgenic and/or genetically modified plant, wherein the plant comprises a sucrose storage organ and is at least three months old;
   b) detecting the amount of a nucleic acid molecule and the amount of mRNA or DNA for BvTST1, BvTST2.2 and BvTST3 in the isolated mRNA or DNA of the at least one leaf;
   c) detecting the amount of the nucleic acid molecule and the amount of mRNA or DNA for BvTST1, BvTST2.2 and BvTST3 in the isolated mRNA of the at least one taproot;
   d) identifying the transgenic and/or genetically modified plant in which the amount of mRNA or DNA for the nucleic acid molecule in the at least one leaf is lower than the amount of mRNA for BvTST1, BvTST2.2 and BvTST3 and the amount of the mRNA or DNA for the nucleic acid molecule in the at least one taproot is higher than the amount of mRNA or DNA for BvTST1, BvTST2.2 and BvTST3; and
   e) cultivating the identified transgenic and/or genetically modified plant, transgenic and/or genetically modified plant part or seeds of the transgenic and/or genetically modified plant, wherein the transgenic and/or genetically modified plant is *Beta vulgaris,*
wherein the nucleic acid molecule encodes a tonoplast proton/sugar antiporter specific for sucrose, wherein the nucleic acid molecule comprises:
   a) the nucleotide sequence of SEQ ID NO: 2 or a nucleotide sequence which is at least 90% identical to SEQ ID NO: 2;
   b) a nucleic acid molecule comprising a nucleotide sequence which is complementary to one of the nucleotide sequences according to a); or
   c) a nucleotide sequence encoding a polypeptide comprising the amino acid sequence of SEQ ID NO: 1 or an amino acid sequence which is at least 90% identical to SEQ ID NO: 1, and
wherein the nucleic acid molecule further comprises at least one heterologous regulatory element.

5. The method of claim 3, wherein the BvTST1 is encoded by the nucleic acid sequence of SEQ ID NO: 4.

6. The method of claim 3, wherein the BvTST2.2 is encoded by the nucleic acid sequence of SEQ ID NO: 6.

7. The method of claim 3, wherein the BvTST3 is encoded by the nucleic acid sequence of SEQ ID NO: 8.

8. A method for identifying a transgenic and/or genetically modified plant, transgenic and/or genetically modified plant part or seeds of the transgenic and/or genetically modified plant wherein the transgenic and/or genetically modified plant comprises a nucleic acid molecule as a transgene and is suitable to generate an increased sucrose concentration in a sucrose storage organ, the method comprising:
   a) isolating DNA or mRNA from the transgenic and/or genetically modified plant, transgenic and/or genetically modified plant part or seeds of the transgenic and/or genetically modified plant, wherein the transgenic and/or genetically modified plant comprises a sucrose storage organ;
   b) detecting the transgene of the nucleic acid molecule in the isolated DNA or mRNA; and
   c) identifying the transgenic and/or genetically modified plant, transgenic and/or genetically modified plant part or seeds of the transgenic and/or genetically modified plant in which the nucleic acid molecule has been detected,
wherein the transgenic and/or genetically modified plant is *Beta vulgaris,*
wherein the nucleic acid molecule encodes a tonoplast proton/sugar antiporter specific for sucrose, wherein the nucleic acid molecule comprises:
   a) the nucleotide sequence of SEQ ID NO: 2 or a nucleotide sequence which is at least 90% identical to SEQ ID NO: 2;
   b) a nucleic acid molecule comprising a nucleotide sequence which is complementary to one of the nucleotide sequences according to a); or
   c) a nucleotide sequence encoding a polypeptide comprising the amino acid sequence of SEQ ID NO: 1 or an amino acid sequence which is at least 90% identical to SEQ ID NO: 1, and
wherein the nucleic acid molecule further comprises at least one heterologous regulatory element.

9. A method for identifying and cultivating a transgenic and/or genetically modified plant, transgenic and/or genetically modified plant part or seeds of the transgenic and/or genetically modified plant wherein the transgenic and/or genetically modified plant is suitable to generate an increased sucrose concentration in a sucrose storage organ, the method comprising:
   a) isolating mRNA or DNA from the transgenic and/or genetically modified plant wherein the transgenic and/or genetically modified plant comprises a sucrose storage organ and is at least three months old;
   b) detecting the amount of a nucleic acid molecule in the isolated mRNA or DNA;
   c) identifying the transgenic and/or genetically modified plant in which the amount of the nucleic acid molecule is higher as compared to a reference plant of the same species or a part thereof cultivated under identical conditions; and
   d) cultivating the identified transgenic and/or genetically modified plant, transgenic and/or genetically modified plant part or seeds of the transgenic and/or genetically modified plant,
wherein the transgenic and/or genetically modified plant is *Beta vulgaris,*
wherein the nucleic acid molecule encodes a tonoplast proton/sugar antiporter specific for sucrose, wherein the nucleic acid molecule comprises:
   a) the nucleotide sequence of SEQ ID NO: 2 or a nucleotide sequence which is at least 95% identical to SEQ ID NO: 2;
   b) a nucleic acid molecule comprising a nucleotide sequence which is complementary to one of the nucleotide sequences according to a); or
   c) a nucleotide sequence encoding a polypeptide comprising the amino acid sequence of SEQ ID NO: 1 or an amino acid sequence which is at least 95% identical to SEQ ID NO: 1, and
wherein the nucleic acid molecule further comprises at least one heterologous regulatory element.

* * * * *

SEQUENCE LISTING

```
<160> NUMBER OF SEQ ID NOS: 33

<210> SEQ ID NO 1
<211> LENGTH: 735
<212> TYPE: PRT
<213> ORGANISM: Beta vulgaris

<400> SEQUENCE: 1

Met Ser Ala Ala Val Leu Val Ala Ile Ala Ala Thr Val Gly Asp Leu
1               5                   10                  15

Leu Tyr Gly Trp Asp Asn Ala Thr Ile Ala Gly Ala Val Leu Tyr Ile
            20                  25                  30

Lys Lys Glu Phe Asn Leu Glu Ser Ser Pro Thr Leu Glu Gly Leu Ile
        35                  40                  45

Val Ala Thr Ser Ile Ile Gly Ala Thr Leu Ile Thr Thr Cys Ser Gly
    50                  55                  60

Pro Ile Ala Asp Arg Leu Gly Arg Arg Pro Met Met Ile Ile Ser Ser
65                  70                  75                  80
```

```
Val Cys Phe Phe Val Ser Ala Leu Ile Met Leu Trp Ser Pro Asn Val
                85                  90                  95

Tyr Val Leu Leu Phe Gly Arg Leu Leu Asp Gly Phe Gly Ser Gly Leu
            100                 105                 110

Ala Val Thr Leu Gly Pro Leu Tyr Ile Ser Glu Thr Ala Pro Thr Asp
        115                 120                 125

Ile Arg Gly Ser Leu Asn Thr Leu Pro Gln Phe Thr Gly Ser Gly Gly
    130                 135                 140

Met Phe Leu Ala Tyr Cys Met Val Phe Gly Met Ser Leu Met Glu Thr
145                 150                 155                 160

Pro Ser Trp Arg Leu Met Leu Gly Ile Leu Phe Val Pro Ser Thr Val
                165                 170                 175

Tyr Phe Leu Leu Thr Val Phe Phe Leu Pro Glu Ser Pro Arg Trp Leu
            180                 185                 190

Val Ser Lys Gly Arg Met Asn Glu Ala Lys Lys Val Leu Gln Trp Leu
        195                 200                 205

Arg Gly Arg Glu Asp Val Phe Ala Glu Met Ala Leu Leu Val Glu Gly
    210                 215                 220

Leu Arg Val Gly Gly Asp Thr Ser Ile Glu Glu Tyr Leu Ile Glu Pro
225                 230                 235                 240

Asp Ala Gly Leu Ala Glu Asp Gln Asp Pro Met Thr Val Lys Asp Gln
                245                 250                 255

Val Arg Leu Tyr Gly Ser Glu Ala Gly Cys Ser Trp Val Ala Arg Pro
            260                 265                 270

Val Thr Gly Gln Ser Met Leu Gly Ile Ala Ser Arg Gln Gly Ser Met
        275                 280                 285

Gln Ser Pro Ser Val Pro Leu Met Asp Pro Leu Val Thr Leu Phe Gly
    290                 295                 300

Ser Val His Glu Lys Leu Pro Glu Gln Gly Ser Met Leu Ser Val Ile
305                 310                 315                 320

Phe Pro Thr Phe Gly Ser Met Phe Ser Met Gly Gly Lys Glu Pro Lys
                325                 330                 335

Asn Glu Glu Trp Asp Asp Glu Asn Thr Ile Gly Asp Asp Asp Tyr
            340                 345                 350

Gly His Asp Asp Glu Asp Tyr Ala Gly Asp Ala Asp Glu Asp Asp Asn
        355                 360                 365

Leu Arg Ser Ser Leu Ile Ser Arg Gln Asp Thr Gly Pro Asp Lys Ala
    370                 375                 380

Met Val Ala Pro Thr Ser Gly Ser Met Phe Ser Met Lys His Ser Ser
385                 390                 395                 400

Trp Leu Gln Gly Ser Glu Ala Ser Gly Ile Gly Gly Gly Trp Gln Leu
                405                 410                 415

Ala Trp Lys Trp Ser Glu Arg Glu Gly Leu Asp Gly Thr Lys Glu Gly
            420                 425                 430

Gly Phe Lys Arg Leu Tyr Leu His Gln Glu Gly Asp Ala Gly Ser Lys
        435                 440                 445

Arg Gly Ser Val Ile Ser Leu Ala Gly Gly Val Ile Gly Asp Asn
    450                 455                 460

Glu Tyr Val Lys Ala Ala Ala Leu Val Ser Gln Pro Ala Leu Tyr Ser
465                 470                 475                 480

Arg Asp Phe Met Asp Arg Asp Ser Ile Gly Pro Ala Met Val His Pro
                485                 490                 495
```

```
Ser Glu Ala Ser Ala Lys Arg Pro Ser Trp Arg Asp Phe Leu Glu Pro
                500                 505                 510

Gly Val Arg Arg Ala Leu Val Val Gly Val Gly Leu Gln Leu Leu Gln
            515                 520                 525

Gln Phe Ala Gly Ile Asn Gly Val Leu Tyr Tyr Thr Pro Gln Ile Leu
        530                 535                 540

Glu Gln Ala Gly Val Gly Asp Leu Leu Ser His Met Gly Ile Gly Ala
545                 550                 555                 560

Ser Ser Ala Leu Leu Leu Ile Ser Ala Leu Thr Thr Leu Leu Met Leu
                565                 570                 575

Pro Ala Ile Ala Val Ala Met Arg Leu Met Asp Leu Ser Gly Arg Arg
            580                 585                 590

Thr Leu Leu Leu Thr Thr Ile Pro Val Leu Phe Leu Ser Leu Val Val
        595                 600                 605

Leu Ile Leu Ala Asn Val Ile Lys Met Asn Thr Thr Val Tyr Ala Val
        610                 615                 620

Val Ser Thr Val Ala Val Val Leu Tyr Phe Cys Phe Val Met Gly
625                 630                 635                 640

Phe Gly Pro Ile Pro Asn Ile Leu Cys Ala Glu Ile Phe Pro Thr Lys
                645                 650                 655

Ile Arg Gly Val Cys Ile Ala Ile Cys Ala Leu Thr Phe Trp Ile Cys
            660                 665                 670

Asp Ile Ile Val Thr Tyr Thr Leu Pro Met Met Leu Lys Ala Val Gly
        675                 680                 685

Leu Ala Gly Leu Phe Gly Phe Tyr Ala Val Val Ile Leu Ile Ala Trp
    690                 695                 700

Ile Phe Ile Phe Leu Lys Val Pro Glu Thr Lys Gly Met Pro Leu Glu
705                 710                 715                 720

Val Ile Thr Glu Phe Phe Ala Leu Gly Ala Arg Gln Ala Ser His
                725                 730                 735

<210> SEQ ID NO 2
<211> LENGTH: 2208
<212> TYPE: DNA
<213> ORGANISM: Beta vulgaris

<400> SEQUENCE: 2
atgagtgcag cagtattagt tgcaattgct gcaacagttg agagatttgct gtatggatgg      60 gataatgcta ctattgctgg ggctgtatta tatattaaga aagagttcaa cttggagagt     120
tctccaacct tggaagggtt aattgtggcc acatcaataa ttggagccac tcttattaca     180
acatgttctg gaccgattgc agatcgtctt ggtcgtcgcc tatgatgat aatttcctca      240 gtttgtttct tgttagtgc cttaataatg ttgtggtctc ccaatgttta tgttttactc      300
ttcggtcggc tattagatgg atttggaagt ggtttggcag tcactcttgg tcctctttat     360
atatcagaga ccgctccaac tgatataaga ggctcactga acacacttcc tcagtttact     420
ggttctggtg gaatgttcct cgcatactgc atggttttcg ggatgtcatt gatggaaaca     480
cctagctgga gattaatgct tgggattctt tttgttccat ctactgttta ttttctatta     540
actgtattct tcttacctga gtctcctcgc tggcttgtta gcaaggacg gatgaatgag      600 gctaaaaagg ttcttcaatg gttgcgaggc aggaagatg tctttgctga tggctctc       660 cttgttgagg tcttagagt tggaggtgat acatcaatag gaatacttt gattgagcca      720 gatgctggac tcgctgagga tcaagatccg atgactgtca aagatcaggt taggctgtat     780
```

```
gggtccgaag caggctgctc ctgggttgcc agaccagtca ctggtcagag tatgctgggt    840
attgcatctc ggcagggaag catgcagagt cctagtgttc ctttaatgga tccccttgta    900
actcttttg gtagtgtaca tgaaaagctt ccagaacaag gaagtatgct agtgtcata    960
ttcccaactt ttggtagtat gtttagtatg ggagggaaag agcccaaaaa tgaagagtgg    1020
gatgatgaaa atactattgg ggatgatgat gattatggtc atgacgatga agattatgca    1080
ggtgatgctg atgaagatga caatttacgt agttcactta tatctcgtca ggatacaggt    1140
ccagacaaag ccatggttgc tcctacttca ggtagcatgt tcagcatgaa gcatagtagt    1200
tggttacaag gaagcgaagc tagtggtatt ggtggtggtt ggcagttagc ttggaaatgg    1260
agcgagagag aaggcttgga tggtacgaag gaaggaggat tcaaaagact ttatctacat    1320
caggaaggtg atgctggatc taaacgaggc tctgttattt ctcttgctgg tggtgaggtt    1380
attggcgaca atgagtatgt gaaggctgct gcactagtaa gtcaacctgc cctttattcg    1440
agggatttca tggatcggga tagtattggt ccagctatgg ttcacccttc cgaggcttct    1500
gcaaaaaggc ctagttggag ggatttttta gagcctggtg tcaggcgtgc attagttgtt    1560
ggtgtcggac ttcaacttct tcaacagttc gctgggataa atggcgttct gtattatact    1620
cctcaaatac tagagcaagc tggggtgggt gatcttcttt cgcatatggg tataggcgct    1680
tcctctgcat tgttactcat cagtgcactc acaactcttt tgatgcttcc tgctatagct    1740
gttgcaatga ggcttatgga tctttctggg agaaggactt gctactaac cacaattccg    1800
gtgttgttct tatcgctcgt tgtcttaata ctcgcaaatg tcataaagat gaacaccact    1860
gtgtatgcag tggtctccac agtcgcggta gttctctact tctgcttctt tgtgatgggg    1920
tttgggccta tcccaaatat cctatgtgca gaaattttcc caaccaagat tcgtggagtc    1980
tgtattgcta tttgtgcact tactttctgg atctgtgata tcatagtcac ctacacactc    2040
cctatgatgc ttaaagctgt tggacttgct ggtctctttg gcttctatgc tgttgtgatt    2100
ttaattgcat ggatatttat attttttgaag gttcctgaaa ccaagggcat gccccttgag    2160
gtaatcactg agttctttgc tctcggtgca agacaagcaa gccactga                2208
```

<210> SEQ ID NO 3  
<211> LENGTH: 735  
<212> TYPE: PRT  
<213> ORGANISM: Beta vulgaris

<400> SEQUENCE: 3

```
Met Lys Gly Ala Val Leu Val Ala Leu Ala Ala Thr Ile Gly Asn Phe
 1               5                  10                  15

Leu Gln Gly Trp Asp Asn Ala Thr Ile Ala Gly Ser Ile Leu Tyr Ile
            20                  25                  30

Lys Lys Glu Leu Glu Leu Ser Thr Ala Met Glu Gly Leu Val Val Ala
        35                  40                  45

Met Ser Leu Ile Gly Ala Thr Val Ile Thr Thr Cys Ser Gly Ala Val
    50                  55                  60

Ser Asp Ala Val Gly Arg Arg Pro Leu Leu Met Leu Ser Ala Ser Leu
65                  70                  75                  80

Tyr Phe Ile Gly Ser Leu Val Met Leu Trp Ser Pro Asn Val Tyr Ile
                85                  90                  95

Leu Leu Leu Ala Arg Leu Leu Asp Gly Phe Gly Ile Gly Leu Ala Val
            100                 105                 110

Thr Leu Val Pro Val Tyr Ile Ser Glu Thr Ser Pro Pro Glu Ile Arg
        115                 120                 125
```

```
Gly Leu Leu Asn Thr Leu Pro Gln Phe Thr Gly Ser Gly Gly Met Phe
    130                 135                 140

Leu Ser Tyr Cys Met Ile Phe Gly Met Ser Leu Met Ala Ser Pro Ser
145                 150                 155                 160

Trp Arg Ile Met Leu Gly Val Leu Gly Ile Pro Ser Val Phe Tyr Leu
                165                 170                 175

Leu Phe Ala Phe Phe Tyr Leu Pro Glu Ser Pro Arg Trp Leu Val Ser
            180                 185                 190

Lys Gly Arg Met Ser Glu Ala Lys Lys Val Leu Lys Arg Leu Arg Gly
        195                 200                 205

Thr Glu Asp Val Ser Gly Glu Leu Ser Leu Leu Val Glu Gly Leu Gly
    210                 215                 220

Val Gly Gly Glu Thr Ser Ile Glu Glu Tyr Ile Val Glu Pro Ala Glu
225                 230                 235                 240

Glu Leu Ala Gly Gly Thr Glu Lys Gly Lys Val Lys Leu Tyr Gly Ala
                245                 250                 255

Ala Glu Gly Leu Ser Trp Ile Ala Lys Pro Val Thr Gly Gln Ser Ala
            260                 265                 270

Val Gly Leu Val Ser Arg His Gly Ser Met Val Gly Leu Val Asp Pro
        275                 280                 285

Leu Val Thr Leu Phe Gly Ser Val His Glu Lys Leu Pro Glu Gln Gly
    290                 295                 300

Asn Met Arg Ser Ala Leu Phe Pro Ser Ile Gly Ser Met Leu Ser Thr
305                 310                 315                 320

Ala Asp Ala His Val His Arg Asp Gln Trp Asp Glu Asn Gln Asp
                325                 330                 335

Val Asp Glu Asp Asp Glu Pro Ile Ala Asp Pro Ala Gly Gly Glu Asp
            340                 345                 350

Phe Asp Asp Asn Asp Leu His Ala Pro Leu Ile Ser Arg Gln Thr Thr
        355                 360                 365

Ser Met Glu Lys Asp Met Gly Leu Pro Pro Val Ser His Gly Thr Val
    370                 375                 380

Met Ser Met Gly Tyr His Gly Ser Leu Phe Gln Gly Ala Gly Glu Thr
385                 390                 395                 400

Ile Thr Thr Thr Gly Ile Gly Gly Gly Trp Gln Leu Ala Trp Thr Leu
                405                 410                 415

Asp Glu Lys Glu Ala Glu Asp Gly Lys Lys Ser Lys Asp Phe Lys Arg
            420                 425                 430

Ile Tyr Leu His Gln Asp Gly Pro Ala Ser Met Arg Gly Ser Leu
        435                 440                 445

Leu Ser Leu Pro Gly Gly Asp Phe Pro Gly Asp Gly Asp Cys Val Gln
    450                 455                 460

Ala Ser Ala Leu Val Ser Asn Pro Ala Leu Tyr Ser Lys Glu Val Leu
465                 470                 475                 480

Gly Gln Ser Pro Ile Gly Pro Ala Met Val His Pro Ala Glu Ile Ala
                485                 490                 495

Ser Gln Gly Pro Thr Trp Lys Ala Leu Leu Asp Pro Gly Val Lys Arg
            500                 505                 510

Ala Leu Ile Val Gly Val Gly Ile Gln Met Leu Gln Gln Phe Ala Gly
        515                 520                 525

Ile Asn Gly Val Leu Tyr Tyr Thr Pro Gln Ile Leu Glu Glu Ala Gly
    530                 535                 540
```

Val Glu Val Leu Leu Ser Asp Leu Gly Ile Ser Ser Thr Ser Ala Ser
545                 550                 555                 560

Phe Leu Ile Ser Ala Leu Thr Thr Phe Leu Met Leu Pro Cys Ile Ala
            565                 570                 575

Val Ala Met Arg Leu Met Asp Ile Ser Gly Arg Arg Ser Leu Leu Leu
        580                 585                 590

Ala Thr Ile Pro Val Leu Ile Ala Ser Leu Val Ile Leu Val Ile Ser
        595                 600                 605

Cys Thr Val Ser Met Gly Ser Val Ile His Ala Val Ile Ser Ile Ile
    610                 615                 620

Cys Val Ile Val Tyr Phe Cys Thr Phe Val Met Ala Tyr Gly Pro Ile
625                 630                 635                 640

Pro Asn Ile Leu Cys Ser Glu Ile Phe Pro Thr Arg Val Arg Gly Val
            645                 650                 655

Cys Ile Ala Ile Cys Gly Leu Val Phe Trp Ile Cys Asp Ile Ile Val
        660                 665                 670

Thr Tyr Ser Leu Pro Val Met Leu Asn Ser Ile Gly Leu Gly Gly Ile
        675                 680                 685

Phe Ala Ile Tyr Ala Val Val Cys Val Ile Ser Leu Val Phe Val Tyr
        690                 695                 700

Leu Lys Val Pro Glu Thr Lys Gly Met Pro Leu Glu Val Ile Thr Glu
705                 710                 715                 720

Phe Phe Ser Val Asp Pro Lys Gln Leu Glu Ala Ala Lys Ala Glu
            725                 730                 735

<210> SEQ ID NO 4
<211> LENGTH: 2208
<212> TYPE: DNA
<213> ORGANISM: Beta vulgaris

<400> SEQUENCE: 4

```
atgaagggtg ctgtgcttgt ggctttggct gctacaattg gtaatttcct acagggttgg      60
gacaatgcaa caattgctgg gtctattctc tacatcaaga agaacttgaa actatccacc     120
gccatggagg gacttgtcgt ggcaatgtca cttattggag ctacggttat acaacgtgcc     180 tcggggccg tatcagatgc tgttggtcga cgtcctttgc tgatgctctc ggcctcactc      240
tactttattg gcagtttggt gatgttatgg tcacctaatg tctatatttt gcttttagcc     300
aggttgttgg atggttttgg aataggggtg gctgtgaccc ttgttcctgt ttatatatca     360
gagacttccc ctccagagat taggggatta ctaaatacac ttcctcaatt cactggctct     420
ggtggaatgt tcttatcata ctgcatgatc tttggaatgt cactcatggc atctcctagc     480
tggagaataa tgcttggtgt tcttgggatc ccttctgttt tttatctttt atttgcattc     540
ttctacttgc ctgaatcccc gcggtggctt gtgagcaaag aaggatgtc tgaagcaaag      600 aaggttttga aaagattacg tggcactgaa gatgtctcag gtgaattgtc tttgctagtt     660
gaagggcttg gtgtcggggg tgaaacttca atagaagagt acattgtaga accagcagaa     720
gagctagcag gtggtactga gaaaggcaaa gtaaagctat acggagcagc agaaggcctt     780
tcttggattg caaacctgt cactggacag agtgctgttg gtcttgtatc ccgtcatgga     840
agcatggtgg gcctagttga tcctctcgtg actctgtttg gaagcgtcca tgaaaagctt     900
cctgaacaag gaaacatgag aagtgcgctt ttcccaagta ttggcagcat gttaagcacg     960
gcagatgctc atgttcacag agatcaatgg gatgaagaaa accaggatgt tgatgaagac    1020
gatgagccaa tcgctgatcc tgcaggaggg gaggattttg atgataatga cttgcatgct    1080
```

-continued

```
ccattgattt cacgtcaaac aacaagcatg gagaaagaca tgggtcttcc tcctgtctct    1140
catggtactg ttatgagcat gggataccat ggcagtcttt ttcaaggtgc tggggaaact    1200
attactacta caggaattgg cggtggttgg caattggcgt ggactttaga tgagaaagaa    1260
gctgaagatg gaaagaaatc taaagacttc aaaaggattt acttgcatca ggatggcggg    1320
ccggcttcta tgcgtggatc acttctatca cttcctggtg gtgatttccc tggagatgga    1380
gattgtgttc aggcttctgc tcttgtaagt aatcctgcac tttattcgaa ggaggttctg    1440
ggtcaaagtc ctattggtcc tgcgatggtt catccagctg aaattgcttc ccaaggacca    1500
acctggaagg ctctccttga tccaggagtc aagcgtgcat tgattgttgg agttggaatt    1560
cagatgcttc aacagttcgc tggtataaat ggcgttctct actataccccc acaaattcta    1620 gaagaggcag gagtagaagt tcttctatct gatctaggga tcagctctac atctgcctca    1680
tttcttatca gtgcattaac gaccttctta atgctgccct gtatcgctgt tgctatgagg    1740
ctcatggata tctctggtag aaggtcactg ttgcttgcta caattcctgt gttgatcgcc    1800
tcattggtta tcctagtaat cagctgcact gttagcatgg gtagtgtaat tcatgctgtc    1860
atctcaatca tctgtgttat tgtctacttc tgcacatttg ttatggctta cggacccata    1920
ccgaatattt tatgttccga gatcttccct actcgagtcc gtggtgtttg tattgctata    1980
tgtggcttgg ttttctggat atgcgacatt attgtcactt actccttgcc cgtcatgctc    2040
aattctattg gtttgggagg catcttcgca atatatgctg tggtttgtgt catctctttg    2100
gtgtttgtct acctcaaagt cccagaaaca aagggtatgc ccttagaagt tatcacagag    2160
ttcttttcag ttgatcctaa acagttagaa gccgctaagg cggagtag                 2208
```

<210> SEQ ID NO 5
<211> LENGTH: 739
<212> TYPE: PRT
<213> ORGANISM: Beta vulgaris

<400> SEQUENCE: 5

```
Met Ser Gly Ala Val Leu Val Ala Ile Ala Ala Ala Val Gly Asn Leu
1               5                  10                  15

Leu Gln Gly Trp Asp Asn Ala Thr Ile Ala Gly Ala Val Leu Tyr Ile
            20                  25                  30

Lys Lys Glu Phe Asn Leu Glu Gly Ala Pro Thr Met Glu Gly Leu Ile
        35                  40                  45

Val Ala Met Ser Leu Ile Gly Ala Thr Ile Ile Thr Thr Cys Ser Gly
    50                  55                  60

Pro Val Ser Asp Arg Phe Gly Arg Arg Pro Met Met Ile Ile Ser Ser
65                  70                  75                  80

Ile Cys Phe Phe Phe Ser Ala Leu Ile Met Leu Trp Ser Pro Asn Val
                85                  90                  95

Tyr Val Leu Leu Leu Gly Arg Leu Leu Asp Gly Phe Ser Gly Leu
            100                 105                 110

Ala Val Thr Leu Val Pro Leu Tyr Ile Ser Glu Thr Ala Pro Thr Asp
        115                 120                 125

Ile Arg Gly Ser Leu Asn Thr Leu Pro Gln Phe Thr Gly Ser Gly Gly
    130                 135                 140

Met Phe Val Ala Tyr Cys Met Val Phe Gly Met Ser Leu Met Glu Lys
145                 150                 155                 160

Pro Ser Trp Arg Leu Met Leu Gly Ile Leu Val Val Pro Ser Ala Leu
                165                 170                 175
```

```
Tyr Phe Ala Leu Thr Val Phe Phe Leu Pro Glu Ser Pro Arg Trp Leu
            180                 185                 190

Val Ser Lys Gly Arg Met Asn Glu Ala Lys Lys Val Leu Gln Arg Leu
            195                 200                 205

Arg Gly Arg Glu Asp Val Ser Ala Glu Met Ala Leu Leu Val Glu Gly
            210                 215                 220

Leu Gly Val Gly Gly Asp Ile Ser Ile Glu Glu Tyr Leu Ile Glu Pro
225                 230                 235                 240

Asp Val Gly Ile Ser Glu Glu Tyr Asp Pro Met Ala Ala Lys Asp Gln
                245                 250                 255

Ile Lys Leu Tyr Gly Ser Asp Ala Gly His Ser Trp Val Ala Arg Pro
            260                 265                 270

Val Thr Gly Gln Ser Met Leu Gly Leu Ala Ser Arg Gln Gly Ser Ile
            275                 280                 285

Gln Asn Pro Ser Val Pro Leu Met Asp Pro Leu Val Thr Leu Phe Gly
            290                 295                 300

Ser Val His Glu Lys Leu Pro Glu Gln Gly Ser Met Arg Ser Ile Ile
305                 310                 315                 320

Phe Pro Thr Phe Gly Ser Met Phe Ser Met Gly Gly Lys Asp Pro Arg
                325                 330                 335

Asn Glu Glu Trp Asp Glu Glu Asn Leu His Gly Asp Asp Asp Tyr
            340                 345                 350

Ala His Asn Asp Asp Asn Asp Asp Tyr Ala Glu Asp Asp Asp Asn
                355                 360                 365

Leu His Ser Pro Leu Ile Ser Arg Gln Ala Thr Gly Thr Asp Lys Ala
            370                 375                 380

Met Val Ala Pro Val Ser Gly Ser Met Phe Ser Met Lys Pro Ser Gly
385                 390                 395                 400

Leu Ile Gln Gly Thr Glu Ala Ser Gly Ile Gly Gly Trp Gln Leu
                405                 410                 415

Ala Trp Gln Trp Ser Glu Lys Glu Gly Ala Asp Gly Arg Lys Glu Gly
            420                 425                 430

Gly Phe Lys Arg Leu Tyr Leu His Gln Glu Gly Asp Met Val Ser Lys
            435                 440                 445

Arg Gly Ser Val Ile Ser Leu Pro Gly Gly Asp Val Thr Gly Glu Thr
450                 455                 460

Glu Tyr Met Lys Ala Ala Ala Leu Val Ser Gln Pro Ala Leu Tyr Ser
465                 470                 475                 480

Arg Glu Leu Met Asn Gln His Thr Ile Gly Pro Ala Met Val His Pro
            485                 490                 495

Ser Glu Thr Ala Ala Lys Gly Ser Ser Trp Arg Asp Leu Leu Glu Pro
            500                 505                 510

Gly Val Arg Arg Ala Leu Ile Val Gly Val Gly Leu Gln Leu Leu Gln
            515                 520                 525

Gln Phe Ser Gly Ile Asn Gly Val Leu Tyr Tyr Thr Pro Gln Ile Leu
            530                 535                 540

Glu Gln Ala Gly Val Gly Asp Leu Leu Ser Asn Met Gly Ile Gly Ala
545                 550                 555                 560

Ser Ser Ala Ser Leu Leu Ile Ser Ala Leu Thr Thr Leu Leu Met Leu
                565                 570                 575

Pro Ser Ile Ala Val Ala Met Arg Leu Met Asp Ile Ser Gly Arg Arg
            580                 585                 590
```

```
Thr Leu Leu Leu Thr Thr Ile Pro Val Leu Phe Leu Ser Leu Val Val
            595                 600                 605

Leu Ile Leu Gly Asn Ile Ile Lys Met Ser Thr Thr Val His Ala Val
        610                 615                 620

Ile Ser Thr Val Ser Val Val Leu Tyr Phe Cys Phe Val Met Gly
625                 630                 635                 640

Phe Gly Pro Ile Pro Asn Ile Leu Cys Ala Glu Ile Phe Pro Thr Arg
                    645                 650                 655

Ile Arg Gly Val Cys Ile Ala Ile Cys Ala Leu Thr Phe Trp Ile Gly
                660                 665                 670

Asp Ile Ile Val Thr Asp Thr Leu Pro Ile Met Leu Asn Ala Val Gly
            675                 680                 685

Leu Ala Gly Val Phe Gly Phe Tyr Ala Val Val Ser Val Ile Ala Trp
        690                 695                 700

Ile Phe Ile Phe Leu Lys Val Pro Glu Thr Lys Gly Met Pro Leu Glu
705                 710                 715                 720

Val Ile Thr Glu Phe Phe Ala Leu Gly Ala Arg Gln Pro Ser Glu Asp
                    725                 730                 735

Lys Asp Asn

<210> SEQ ID NO 6
<211> LENGTH: 2220
<212> TYPE: DNA
<213> ORGANISM: Beta vulgaris

<400> SEQUENCE: 6
atgagtggag cggtattagt tgcaattgct gcggcagttg gaatttact acaaggatgg      60 gataatgcta ctattgctgg ggctgtgttg tatattaaga aagaattcaa cttggagggc    120
gcgccaacca tggaaggctt aattgtggcc atgtcactta ttggagccac tattatcaca    180
acatgctctg gaccagtttc agatcgcttt gggcgtcgcc ctatgatgat aatctcctct    240
atatgtttct ttttagtgc cctaataatg ttgtggtctc ccaatgttta tgtcctactc     300
ttgggtcgat tattagatgg atttggaagt ggtttggctg tcactcttgt tcctctttat    360
atatcagaga cagctccaac tgatataagg ggttcattga atacacttcc tcaatttact    420
ggttcgggtg gaatgttttgt tgcgtactgt atggtgtttg gatgtctttt aatggaaaaa    480
cctagctgga gattgatgct tgggattctt gttgttccat ctgctctta ttttgcatta    540 actgtattct tcttacccga gtctcctcga tggcttgtta gtaaaggacg aatgaatgag    600
gccaaaaagg ttcttcaacg attgcggggc agggaagatg tctctgctga gatggctctg    660
cttgttgagg tcttggagt tggaggtgac atatcaatag aagaatactt aattgagcca    720
gatgttggca tcagcgagga atatgatccg atggctgcca aagatcagat taaattatat    780
gggtcagatg caggccactc ttgggttgcc agaccagtca ccggccagag tatgctgggc    840
cttgcatctc gtcagggaag cattcagaac cctagtgttc ccttaatgga ccccctggtc    900
acgcttttcg gtagtgtaca tgagaagctt ccagaacaag aagcatgcg aagtattatt    960 ttcccgactt tggtagtat gtttagtatg ggaggcaaag accctagaaa tgaagagtgg   1020
gatgaggaga atcttcatgg ggatgatgat gattatgccc ataatgatga tgacaatgat   1080
gattatgctg aagatgatga caatttacat agtccactta tatctcgtca ggctacaggt   1140
acagacaaag ctatggttgc tccagttttca ggtagcatgt tcagcatgaa acctagtggt   1200
ttaatacaag gaactgaagc tagtggaatt ggtggtggtt ggcagctggc ttggcaatgg   1260
```

```
agtgagaaag aaggtgcaga tgggaggaag gagggaggat tcaaaagact ttacttacat   1320
caggaaggtg atatggtatc taaacgagga tctgtaatct ctcttcctgg cggtgatgtt   1380
actggagaga cagagtatat gaaggctgct gcactagtga gtcaacctgc cctctattcg   1440
agggagttga tgaatcagca tactattgga ccagctatgg ttcatccttc tgagactgct   1500
gcaaaagggt ctagctggag ggacctttta gaacctggtg tcaggcgtgc attgattgtt   1560
ggtgtcgggc tccaacttct tcagcagttt tctggtataa atgggttct gtattacact    1620 cctcaaatac tagagcaagc tggggttggt gatcttcttt caaacatggg tattggcgct   1680
tcctctgcat cattgctcat cagtgcactc acaactcttt tgatgcttcc ttccatagct   1740
gttgcaatga ggcttatgga tatttccggg aggaggactt tgctgcttac cacaattccg   1800
gtgttgttcc tttcgctcgt cgtcctaata ctcggaaata tcataaagat gagcactact   1860
gtgcacgcag tgatctcaac agtctccgta gttctctact tctgcttctt tgtgatgggc   1920
tttggcccaa tcccaaatat cctatgcgcg gaaattttcc caaccaggat tcgtggtgtc   1980
tgcattgcta tttgtgcact taccttttgg atcggagata ttatagttac tgacacactt   2040
cctataatgc tcaatgctgt tggacttgct ggtgtctttg gcttctatgc tgtcgttagt   2100
gtaattgctt ggatttttat ctttctaaag gttcccgaaa ccaagggcat gcctctcgag   2160
gtcattactg agttctttgc tctcggggca agacaacctt ctgaagacaa ggacaactga   2220
```

```
<210> SEQ ID NO 7
<211> LENGTH: 728
<212> TYPE: PRT
<213> ORGANISM: Beta vulgaris

<400> SEQUENCE: 7

Met Arg Gly Ala Val Phe Ala Ala Leu Ala Ala Thr Met Gly Asn Leu
1               5                   10                  15

Leu Gln Gly Trp Asp Asn Ala Thr Ile Ala Gly Ala Val Ile Tyr Ile
            20                  25                  30

Lys Arg Glu Phe Ser Leu Glu Thr Gln Pro Thr Leu Glu Gly Leu Ile
        35                  40                  45

Val Ala Met Ser Leu Ile Gly Ala Thr Val Ile Thr Thr Phe Ser Gly
    50                  55                  60

Pro Val Ser Asp Ser Val Gly Arg Arg Pro Met Leu Ile Ile Ser Ser
65                  70                  75                  80

Ile Leu Tyr Phe Leu Gly Gly Leu Val Met Leu Trp Ser Pro Asn Val
                85                  90                  95

Tyr Val Leu Leu Leu Gly Arg Leu Leu Asp Gly Phe Gly Val Gly Leu
            100                 105                 110

Ala Val Thr Leu Val Pro Val Tyr Ile Ser Glu Thr Ala Pro Pro Glu
        115                 120                 125

Ile Arg Gly Gln Leu Asn Thr Leu Pro Gln Phe Thr Gly Ser Gly Gly
    130                 135                 140

Met Phe Leu Ser Tyr Cys Met Val Phe Gly Met Ser Leu Met Glu Ala
145                 150                 155                 160

Pro Arg Trp Arg Leu Met Leu Gly Val Ile Ser Ile Pro Ser Leu Leu
                165                 170                 175

Tyr Leu Gly Leu Met Val Phe Tyr Leu Pro Glu Ser Pro Arg Trp Leu
            180                 185                 190

Val Ser Lys Gly Lys Met His Glu Ala Lys Lys Val Leu Gln Lys Leu
        195                 200                 205
```

```
Arg Gly Arg Glu Asp Val Thr Gly Glu Met Ala Leu Leu Ile Glu Gly
    210                 215                 220

Leu Gly Thr Gly Lys Asn Thr Ser Ile Glu Glu Tyr Val Ile Gly Pro
225                 230                 235                 240

Ala Asn Asp Glu Glu Ala Thr Thr Asp Lys Asp Gln Ile Lys Leu Tyr
                245                 250                 255

Gly Ala Glu Gln Gly Gln Ser Trp Ile Ala Lys Pro Val Arg Gly Gln
                260                 265                 270

Ser Thr Leu Gly Met Val Ser Arg Tyr Gly Ser Met Ala Gln Gln Gly
            275                 280                 285

Ser Met Ala Asn Met Met Asp Pro Leu Val Thr Leu Phe Gly Ser Val
        290                 295                 300

His Glu Lys Leu Pro Gln Ser Gly Ser Met Arg Ser Ala Ile Phe Pro
305                 310                 315                 320

Asn Phe Gly Ser Met Phe Ser Thr Ala Ala Asp Asp His Val Lys His
                325                 330                 335

Val Asn Trp Glu Val Glu Ser Arg Asp Glu Asp Ser Ser Ser Asp Val
                340                 345                 350

Gly His Asp Asp Ser Asp Asp Asn Leu Arg Ser Pro Leu Leu Ser Pro
            355                 360                 365

His Ala Pro Gly Ala Glu Lys Asp Ala Val Pro Pro Leu Asn Gly Asn
        370                 375                 380

Ser Met Leu Met Gln Ser Gly Glu Leu Val Asn Ser Thr Gly Ile Gly
385                 390                 395                 400

Gly Gly Trp Gln Leu Ala Tyr Lys Lys Ala Glu Asp Gly Gly Glu Leu
                405                 410                 415

Lys Arg Val Tyr Leu His Gln Glu Pro Gly Met Gly Ser Met Arg Gly
            420                 425                 430

Ser Met Arg Gly Ser Met Arg Gly Ser Val Leu Ser Leu His Pro Ser
        435                 440                 445

Asp Ile Pro Glu Gly Gln Leu Val Pro Ala Ala Gly Leu Val Ser Gln
    450                 455                 460

Ser Thr Leu Gln Ile Lys Asp Phe Lys Gly Glu Ser Pro Phe Glu Gly
465                 470                 475                 480

Gly Asp Ile Arg Pro Ser Ala Ala Ala Thr Lys Gly Pro Ser Trp Arg
                485                 490                 495

Glu Leu Leu Glu Pro Gly Val Lys Arg Ala Leu Leu Val Gly Met Gly
            500                 505                 510

Met Gln Ile Leu Gln Gln Phe Ser Gly Ile Asn Gly Val Leu Tyr Tyr
        515                 520                 525

Thr Pro Gln Ile Leu Ser Gln Ala Gly Val Asp Val Leu Leu Ser Glu
    530                 535                 540

Leu Gly Ile Gly Ser Asp Ser Ala Ser Leu Leu Ile Ser Gly Leu Thr
545                 550                 555                 560

Thr Leu Leu Met Leu Pro Ser Ile Gly Leu Ala Met Arg Leu Met Asp
                565                 570                 575

Ile Ser Gly Arg Arg Phe Leu Leu Leu Asn Thr Leu Pro Val Leu Ile
            580                 585                 590

Gly Ser Leu Ile Ile Leu Val Leu Ser Asn Val Ile Glu Met Gly Thr
        595                 600                 605

Val Leu His Ala Thr Leu Ser Thr Ile Ser Val Val Tyr Phe Cys
    610                 615                 620

Cys Phe Val Met Gly Phe Gly Pro Ile Pro Asn Ile Leu Cys Ser Glu
```

```
                625                630                635                640
Ile Phe Pro Thr Arg Val Arg Gly Leu Cys Ile Ala Ile Cys Ser Leu
                    645                650                655

Thr Phe Trp Phe Gly Asp Ile Ile Val Thr Tyr Ser Leu Pro Ala Leu
                660                665                670

Leu Ser Ser Ile Gly Leu Ala Gly Val Phe Gly Ile Tyr Ala Val Val
                675                680                685

Cys Ile Val Ser Trp Phe Phe Val Tyr Phe Met Val Pro Glu Thr Lys
            690                695                700

Gly Met Pro Leu Glu Val Ile Ser Glu Phe Phe Asn Val Gly Ala Arg
705                710                715                720

Gln Ala Glu Ala Glu Lys Asn Met
                725

<210> SEQ ID NO 8
<211> LENGTH: 2187
<212> TYPE: DNA
<213> ORGANISM: Beta vulgaris

<400> SEQUENCE: 8
```

| | | | | | |
|---|---|---|---|---|---|
| atgagaggag | ctgtatttgc | agcacttgct | gccacaatgg | gtaacttgtt | gcaagggtgg | 60 |
| gataatgcca | ccatagcagg | agctgttata | tacatcaaga | gggaattcag | cctcgaaaca | 120 |
| caaccaacct | tggaggggct | aattgtggcc | atgtcgctta | ttggggccac | agtgatcaca | 180 |
| accttctcag | gtcccgtttc | agattcagtt | gggcgtcgtc | caatgctaat | catctcatca | 240 |
| atattatact | ttcttggtgg | cttggttatg | ctatggtctc | ctaatgtata | tgtcttgctc | 300 |
| ttgggaaggc | ttttggatgg | ttttggtgtt | ggtctagcag | ttactcttgt | gccagtatat | 360 |
| atatcagaga | ctgcaccccc | agaaatcaga | ggacagttga | ataccctccc | acagttcact | 420 |
| ggctcaggag | ggatgttctt | gtcttactgt | atggtatttg | gcatgtcttt | gatggaagca | 480 |
| cctagatgga | gattgatgct | cggtgttatt | tcaatcccgt | cacttttgta | tcttggattg | 540 |
| atggtgtttt | atttgcctga | gtctcctagg | tggctcgtca | gcaaaggaaa | gatgcatgag | 600 |
| gctaagaaag | tcttacaaaa | attgcgcggc | agggaagatg | tcactggtga | gatggcattg | 660 |
| cttatagaag | ggcttggaac | tgggaaaaat | acatccatcg | aagagtatgt | gataggccca | 720 |
| gcaaatgatg | aagaagccac | cacagataaa | gatcaaatca | gctatatggt | gctgagcaa | 780 |
| ggccaatctt | ggatagccaa | accagtcaga | ggtcaaagca | cgcttggcat | ggtttctcgt | 840 |
| tatggaagca | tggctcagca | gggaagtatg | gcaaacatga | tggatcctct | cgtcactttg | 900 |
| tttggtagtg | ttcatgaaaa | gcttccccaa | tcagggagca | tgcggagtgc | aatattccct | 960 |
| aactttggga | gcatgttcag | tactgctgct | gatgaccatg | ttaaacatgt | aaattgggag | 1020 |
| gtggagagcc | gagatgagga | ctcctcatct | gatgttggcc | atgatgactc | tgatgataat | 1080 |
| ctgaggagtc | cactgctttc | acctcatgcc | cctggagcag | aaaaggatgc | agttcctcca | 1140 |
| ttaaatggca | acagcatgct | gatgcaaagt | ggtgaattag | tcaatagtac | aggtataggt | 1200 |
| ggaggttggc | agttagcgta | caagaaagca | gaagatggtg | gtgaactaaa | aagggtttat | 1260 |
| ctccatcaag | aaccaggaat | ggggtctatg | cgtggatcta | tgcgtgggtc | tatgcgtggg | 1320 |
| tctgtccttt | cactgcatcc | ttctgatatt | cctgaaggtc | agcttgttcc | agctgctggt | 1380 |
| cttgtaagcc | agtccaccct | tcaaatcaag | gatttcaagg | agaatctccc | ttttgaggga | 1440 |
| ggtgatatac | gaccttctgc | agctgctaca | aagggccaa | gctggagaga | gcttcttgaa | 1500 |
| ccaggggtta | agcgtgcatt | gttggttgga | atgggaatgc | agatacttca | acagttctct | 1560 |

```
gggatcaatg gagttctcta ctacacccct caaattcttt cacaagcagg agtggacgtt   1620
ctcctatcag aattagggat tggttcagac tccgcttctc ttcttataag tggtttgacg   1680
acattgttga tgcttcctag cataggcctt gcaatgaggc tgatggatat ctctgggaga   1740
aggtttcttt tactaaacac acttcccgtc ttgataggat ctctcattat acttgtactt   1800
tccaatgtta tcgagatggg aaccgtctta cacgcgacat tatctactat cagtgttgta   1860
gtctacttct gctgctttgt catgggtttt ggccccattc caaatatcct ctgctctgaa   1920
atcttcccta ctcgtgtccg tggcctttgc attgccatat gttctcttac cttctggttt   1980
ggagatatca ttgtcacgta ctctctccca gctttgctct cctctatagg gctcgccgga   2040
gtatttggca tctatgccgt ggtttgcatc gtctcttggt tctttgttta tttcatggta   2100
cctgaaacaa agggcatgcc ccttgaagtt atcagtgagt tcttcaatgt gggtgcaagg   2160
caagctgaag ctgagaaaaa tatgtga                                       2187
```

<210> SEQ ID NO 9
<211> LENGTH: 734
<212> TYPE: PRT
<213> ORGANISM: Arabidopsis thaliana
<400> SEQUENCE: 9

```
Met Lys Gly Ala Thr Leu Val Ala Leu Ala Ala Thr Ile Gly Asn Phe
1               5                   10                  15

Leu Gln Gly Trp Asp Asn Ala Thr Ile Ala Gly Ala Met Val Tyr Ile
            20                  25                  30

Asn Lys Asp Leu Asn Leu Pro Thr Ser Val Gln Gly Leu Val Val Ala
        35                  40                  45

Met Ser Leu Ile Gly Ala Thr Val Ile Thr Cys Ser Gly Pro Ile
    50                  55                  60

Ser Asp Trp Leu Gly Arg Arg Pro Met Leu Ile Leu Ser Ser Val Met
65                  70                  75                  80

Tyr Phe Val Cys Gly Leu Ile Met Leu Trp Ser Pro Asn Val Tyr Val
                85                  90                  95

Leu Cys Phe Ala Arg Leu Leu Asn Gly Phe Gly Ala Gly Leu Ala Val
            100                 105                 110

Thr Leu Val Pro Val Tyr Ile Ser Glu Thr Ala Pro Pro Glu Ile Arg
        115                 120                 125

Gly Gln Leu Asn Thr Leu Pro Gln Phe Leu Gly Ser Gly Met Phe
    130                 135                 140

Leu Ser Tyr Cys Met Val Phe Thr Met Ser Leu Ser Asp Ser Pro Ser
145                 150                 155                 160

Trp Arg Ala Met Leu Gly Val Leu Ser Ile Pro Ser Leu Leu Tyr Leu
                165                 170                 175

Phe Leu Thr Val Phe Tyr Leu Pro Glu Ser Pro Arg Trp Leu Val Ser
            180                 185                 190

Lys Gly Arg Met Asp Glu Ala Lys Arg Val Leu Gln Gln Leu Cys Gly
        195                 200                 205

Arg Glu Asp Val Thr Asp Glu Met Ala Leu Leu Val Glu Gly Leu Asp
    210                 215                 220

Ile Gly Gly Glu Lys Thr Met Glu Asp Leu Leu Val Thr Leu Glu Asp
225                 230                 235                 240

His Glu Gly Asp Asp Thr Leu Glu Thr Val Asp Glu Asp Gly Gln Met
                245                 250                 255
```

Arg Leu Tyr Gly Thr His Glu Asn Gln Ser Tyr Leu Ala Arg Pro Val
                260                 265                 270

Pro Glu Gln Asn Ser Ser Leu Gly Leu Arg Ser Arg His Gly Ser Leu
            275                 280                 285

Ala Asn Gln Ser Met Ile Leu Lys Asp Pro Leu Val Asn Leu Phe Gly
        290                 295                 300

Ser Leu His Glu Lys Met Pro Glu Ala Gly Gly Asn Thr Arg Ser Gly
305                 310                 315                 320

Ile Phe Pro His Phe Gly Ser Met Phe Ser Thr Thr Ala Asp Ala Pro
                325                 330                 335

His Gly Lys Pro Ala His Trp Glu Lys Asp Ile Glu Ser His Tyr Asn
            340                 345                 350

Lys Asp Asn Asp Asp Tyr Ala Thr Asp Asp Ala Gly Asp Asp Asp
        355                 360                 365

Asp Ser Asp Asn Asp Leu Arg Ser Pro Leu Met Ser Arg Gln Thr Thr
370                 375                 380

Ser Met Asp Lys Asp Met Ile Pro His Pro Thr Ser Gly Ser Thr Leu
385                 390                 395                 400

Ser Met Arg Arg His Ser Thr Leu Met Gln Gly Asn Gly Glu Ser Ser
            405                 410                 415

Met Gly Ile Gly Gly Gly Trp His Met Gly Tyr Arg Tyr Glu Asn Asp
        420                 425                 430

Glu Tyr Lys Arg Tyr Tyr Leu Lys Glu Asp Gly Ala Glu Ser Arg Arg
            435                 440                 445

Gly Ser Ile Ile Ser Ile Pro Gly Gly Pro Asp Gly Gly Ser Tyr
450                 455                 460

Ile His Ala Ser Ala Leu Val Ser Arg Ser Val Leu Gly Pro Lys Ser
465                 470                 475                 480

Val His Gly Ser Ala Met Val Pro Pro Glu Lys Ile Ala Ala Ser Gly
            485                 490                 495

Pro Leu Trp Ser Ala Leu Leu Glu Pro Gly Val Lys Arg Ala Leu Val
        500                 505                 510

Val Gly Val Gly Ile Gln Ile Leu Gln Gln Phe Ser Gly Ile Asn Gly
        515                 520                 525

Val Leu Tyr Tyr Thr Pro Gln Ile Leu Glu Arg Ala Gly Val Asp Ile
        530                 535                 540

Leu Leu Ser Ser Leu Gly Leu Ser Ser Ile Ser Ala Ser Phe Leu Ile
545                 550                 555                 560

Ser Gly Leu Thr Thr Leu Leu Met Leu Pro Ala Ile Val Val Ala Met
            565                 570                 575

Arg Leu Met Asp Val Ser Gly Arg Arg Ser Leu Leu Leu Trp Thr Ile
        580                 585                 590

Pro Val Leu Ile Val Ser Leu Val Val Leu Val Ile Ser Glu Leu Ile
        595                 600                 605

His Ile Ser Lys Val Val Asn Ala Ala Leu Ser Thr Gly Cys Val Val
        610                 615                 620

Leu Tyr Phe Cys Phe Phe Val Met Gly Tyr Gly Pro Ile Pro Asn Ile
625                 630                 635                 640

Leu Cys Ser Glu Ile Phe Pro Thr Arg Val Arg Gly Leu Cys Ile Ala
                645                 650                 655

Ile Cys Ala Met Val Phe Trp Ile Gly Asp Ile Ile Val Thr Tyr Ser
            660                 665                 670

Leu Pro Val Leu Leu Ser Ser Ile Gly Leu Val Gly Val Phe Ser Ile

```
           675                 680                 685
Tyr Ala Ala Val Cys Val Ile Ser Trp Ile Phe Val Tyr Met Lys Val
            690                 695                 700

Pro Glu Thr Lys Gly Met Pro Leu Glu Val Ile Thr Asp Tyr Phe Ala
705                 710                 715                 720

Phe Gly Ala Gln Ala Gln Ala Ser Ala Pro Ser Lys Asp Ile
                725                 730

<210> SEQ ID NO 10
<211> LENGTH: 1698
<212> TYPE: DNA
<213> ORGANISM: Arabidopsis thaliana

<400> SEQUENCE: 10
atggcggtta agcacggcgt cgacggcgac ggcagcgaaa tcgaatcgag aactctggcg      60
gtagatcgaa aaagcggttt ctgcgaatca acatcgatat tctacagcaa acgtgagcca     120
atggctctcc cgccaaacca atttctcgac gtcacgtctt tcattgcatc acagcctcat     180
cgcggcaaaa ccgtattcgt cgacgccgta accggtcgtc gactaagctt ccctgagctc     240
tggctcggtg tcgaaagagt cgcgggttgt ctttacgcat taggtgtacg caaaggaaat     300
gtcgtcatta tactctctcc aaactcaatc ctcttcccga tcgtctccct ctccgtaatg     360
tcactcggcg caatcataac caccgctaat ccgatcaaca cgtccgacga aatctccaaa     420
cagataggcg attcgcgtcc tgttctcgcc ttcaccacat gcaaactcgt ctccaaactc     480
gccgccgcgt cgaattttaa tctcccggtg gttctcatgg acgactacca cgttccttcg     540
caaagttacg gtgaccgcgt gaaactagtc gggaggttag agacgatgat tgaaacagaa     600
ccgagtgagt cacgagttaa gcaacgagtc aaccaggacg cacggcggc tctgttatac      660 tcatcaggta cgacggggac gagtaaagga gtaatgctga gtcaccgtaa cctaatcgca     720
ttggtacaag cataccgggc ccggttcggt ttagagcagc gaaccatttg cacaatccca     780
atgtgtcaca tcttcggatt cggtggtttc gcgacggggc taatcgcgtt aggatggaca     840
atcgttgttc ttcctaaatt cgacatggct aagcttctct cggcggtgga gactcatcgt     900
tcttcgtacc tttctcttgt accgccgatt gtagtagcta tggttaacgg agcaaatgag     960
attaattcca gtatgatct gagctcgttg cacactgtgg tggctggagg agctccgttg    1020
agtagagagg tgacggagaa gttcgttgag aattatccca aggttaagat cctacaaggg    1080
tatggtttga ctgagtcaac ggctatagct gcttctatgt ttaataaaga ggagactaag    1140
aggtatggag cttctggctt actggctccg aatgtggaag gtaagattgt ggatccggat    1200
acgggtcggg ttttgggtgt gaatcaaacg ggtgagctgt ggattcgaag tcctactgtg    1260
atgaaaggtt atttcaagaa taagaagct actgcttcta ccattgattc agaaggatgg    1320
ttgaaaactg gagatttgtg ttacattgac ggtgatgggt ttgtctttgt tgttgataga    1380
ttaaaggagc tcatcaaatg caatggttat caggttgctc cagctgaact agaggcattg    1440
ttgcttgctc atccagagat tgctgatgca gcagtaatac ccatccctga catgaaagct    1500
gggcaatatc caatggcata tatcgtaaga aaagttggaa gtaacttatc cgagagcgaa    1560
atcatgggat ttgtcgcaaa acaggtatca ccgtacaaga agattcgcaa agtcacattt    1620
ttggcttcaa tccccaaaaa tccttcgggc aagattttaa gaagagaact tacaaagctc    1680
acaacttcaa aactctag                                                  1698

<210> SEQ ID NO 11
```

```
<211> LENGTH: 739
<212> TYPE: PRT
<213> ORGANISM: Arabidopsis thaliana

<400> SEQUENCE: 11

Met Ser Gly Ala Val Leu Val Ala Ile Ala Ala Val Gly Asn Leu
1               5                   10                  15

Leu Gln Gly Trp Asp Asn Ala Thr Ile Ala Gly Ala Val Leu Tyr Ile
                20                  25                  30

Lys Lys Glu Phe Asn Leu Glu Ser Asn Pro Ser Val Glu Gly Leu Ile
            35                  40                  45

Val Ala Met Ser Leu Ile Gly Ala Thr Leu Ile Thr Thr Cys Ser Gly
50                  55                  60

Gly Val Ala Asp Trp Leu Gly Arg Arg Pro Met Leu Ile Leu Ser Ser
65                  70                  75                  80

Ile Leu Tyr Phe Val Gly Ser Leu Val Met Leu Trp Ser Pro Asn Val
                85                  90                  95

Tyr Val Leu Leu Leu Gly Arg Leu Leu Asp Gly Phe Gly Val Gly Leu
                100                 105                 110

Val Val Thr Leu Val Pro Ile Tyr Ile Ser Glu Thr Ala Pro Pro Glu
            115                 120                 125

Ile Arg Gly Leu Leu Asn Thr Leu Pro Gln Phe Thr Gly Ser Gly Gly
130                 135                 140

Met Phe Leu Ser Tyr Cys Met Val Phe Gly Met Ser Leu Met Pro Ser
145                 150                 155                 160

Pro Ser Trp Arg Leu Met Leu Gly Val Leu Phe Ile Pro Ser Leu Val
                165                 170                 175

Phe Phe Phe Leu Thr Val Phe Phe Leu Pro Glu Ser Pro Arg Trp Leu
                180                 185                 190

Val Ser Lys Gly Arg Met Leu Glu Ala Lys Arg Val Leu Gln Arg Leu
            195                 200                 205

Arg Gly Arg Glu Asp Val Ser Gly Glu Met Ala Leu Leu Val Glu Gly
210                 215                 220

Leu Gly Ile Gly Gly Glu Thr Thr Ile Glu Glu Tyr Ile Ile Gly Pro
225                 230                 235                 240

Ala Asp Glu Val Thr Asp Asp His Asp Ile Ala Val Asp Lys Asp Gln
                245                 250                 255

Ile Lys Leu Tyr Gly Ala Glu Glu Gly Leu Ser Trp Val Ala Arg Pro
            260                 265                 270

Val Lys Gly Gly Ser Thr Met Ser Val Leu Ser Arg His Gly Ser Thr
        275                 280                 285

Met Ser Arg Arg Gln Gly Ser Leu Ile Asp Pro Leu Val Thr Leu Phe
290                 295                 300

Gly Ser Val His Glu Lys Met Pro Asp Thr Gly Ser Met Arg Ser Ala
305                 310                 315                 320

Leu Phe Pro His Phe Gly Ser Met Phe Ser Val Gly Gly Asn Gln Pro
                325                 330                 335

Arg His Glu Asp Trp Asp Glu Glu Asn Leu Val Gly Glu Gly Glu Asp
            340                 345                 350

Tyr Pro Ser Asp His Gly Asp Ser Glu Asp Leu His Ser Pro
        355                 360                 365

Leu Ile Ser Arg Gln Thr Thr Ser Met Glu Lys Asp Met Pro His Thr
370                 375                 380

Ala His Gly Thr Leu Ser Thr Phe Arg His Gly Ser Gln Val Gln Gly
```

```
                385                 390                 395                 400
        Ala Gln Gly Glu Gly Ala Gly Ser Met Gly Ile Gly Gly Trp Gln
                        405                 410                 415

Val Ala Trp Lys Trp Thr Glu Arg Glu Asp Glu Ser Gly Gln Lys Glu
                        420                 425                 430

Gly Gly Phe Lys Arg Ile Tyr Leu His Gln Glu Gly Phe Pro Gly Ser
                        435                 440                 445

Arg Arg Gly Ser Ile Val Ser Leu Pro Gly Gly Asp Gly Thr Gly Glu
                450                 455                 460

Ala Asp Phe Val Gln Ala Ser Ala Leu Val Ser Gln Pro Ala Leu Tyr
        465                 470                 475                 480

Ser Lys Asp Leu Leu Lys Glu His Thr Ile Gly Pro Ala Met Val His
                        485                 490                 495

Pro Ser Glu Thr Thr Lys Gly Ser Ile Trp His Asp Leu His Asp Pro
                        500                 505                 510

Gly Val Lys Arg Ala Leu Val Val Gly Val Gly Leu Gln Ile Leu Gln
                        515                 520                 525

Gln Phe Ser Gly Ile Asn Gly Val Leu Tyr Tyr Thr Pro Gln Ile Leu
                    530                 535                 540

Glu Gln Ala Gly Val Gly Ile Leu Leu Ser Asn Met Gly Ile Ser Ser
        545                 550                 555                 560

Ser Ser Ala Ser Leu Leu Ile Ser Ala Leu Thr Thr Phe Val Met Leu
                        565                 570                 575

Pro Ala Ile Ala Val Ala Met Arg Leu Met Asp Leu Ser Gly Arg Arg
                        580                 585                 590

Thr Leu Leu Leu Thr Thr Ile Pro Ile Leu Ile Ala Ser Leu Leu Val
                    595                 600                 605

Leu Val Ile Ser Asn Leu Val His Met Asn Ser Ile Val His Ala Val
                    610                 615                 620

Leu Ser Thr Val Ser Val Val Leu Tyr Phe Cys Phe Phe Val Met Gly
        625                 630                 635                 640

Phe Gly Pro Ala Pro Asn Ile Leu Cys Ser Glu Ile Phe Pro Thr Arg
                        645                 650                 655

Val Arg Gly Ile Cys Ile Ala Ile Cys Ala Leu Thr Phe Trp Ile Cys
                        660                 665                 670

Asp Ile Ile Val Thr Tyr Ser Leu Pro Val Leu Leu Lys Ser Ile Gly
                        675                 680                 685

Leu Ala Gly Val Phe Gly Met Tyr Ala Ile Val Cys Cys Ile Ser Trp
                        690                 695                 700

Val Phe Val Phe Ile Lys Val Pro Glu Thr Lys Gly Met Pro Leu Glu
        705                 710                 715                 720

Val Ile Thr Glu Phe Phe Ser Val Gly Ala Arg Gln Ala Glu Ala Ala
                        725                 730                 735

Lys Asn Glu

<210> SEQ ID NO 12
<211> LENGTH: 2220
<212> TYPE: DNA
<213> ORGANISM: Arabidopsis thaliana

<400> SEQUENCE: 12
atgagtggag ctgtgcttgt tgctattgct gctgctgttg gcaacttgtt acaaggatgg      60
gataacgcaa ctattgcagg agctgtgttg tacataaaaa aggagtttaa tttggagagt     120
```

```
aatccatcag tggaaggtct aattgtggcg atgtcactta ttggtgctac tctgattaca      180
acatgctctg gagggtagc tgattggctt ggtcgccgtc ccatgctaat attgtcctca      240
attctctact tgttggttc tctagtaatg ctatggtctc cgaatgttta tgtgttgctc      300
ttaggaaggt tgttagatgg atttgggtt ggtcttgtgg tcacacttgt tcctatttat      360
atatctgaga ctgcaccacc tgagattagg ggactgttga atacgctacc gcagttcact      420
ggctctggag gatgttctt atcttactgt atggttttcg gaatgtcgtt gatgccatca      480
cctagctgga gattgatgct tggtgtcctt ttcatccctt cccttgtctt tttcttcctc      540
acggtcttct tcttgcccga gtccccaagg tggctcgtga gcaaaggtcg aatgcttgaa      600
gcaaagcggg ttcttcagag actgcgtggt cgcgaagatg tgtctggtga gatggctttg      660
ttggttgagg tcttggaat tggaggtgaa acaaccatag aggaatatat aattggtccc      720
gcggatgaag ttactgatga tcatgatata gctgtggata aggatcaaat taagttatat      780
ggtgcagaag aagggctgag ttgggttgct aggccagtca aggaggaag cactatgagt      840
gttttgtctc gccatggaag tacaatgagc aggaggcaag gctcattgat tgatcctctt      900
gtcacactgt ttgggagcgt tcacgagaag atgccggaca ctggaagcat gaggagtgcc      960
ttgttcccac attttgggag tatgttcagt gttggaggga tcaaccaag acatgaagat     1020
tgggatgaag agaatcttgt tggagaaggt gaggattatc catccgacca tggagatgat     1080
tctgaagatg atcttcattc tccgttgatc tcacgtcaaa cgacaagcat ggagaaagac     1140
atgcctcaca ctgctcatgg aactctttct accttcagac atggaagtca agtgcaggga     1200
gctcaagggg aaggagcggg tagtatggga attggaggtg gatggcaagt ggcatggaaa     1260
tggacggaaa gagaagatga atcgggacag aaagaaggtg ggtttaaacg gatatacttg     1320
catcaagaag gtttcccagg atctcgacgt ggctcaattg tttcattgcc tggtggtgat     1380
ggaaccggtg aggcagattt tgtacaagcg tctgctttgg ttagccaacc agctctttat     1440
tccaaagacc ttctcaaaga acatacaatt ggtcctgcta tggtacatcc atccgaaaca     1500
actaaaggt caatttggca tgatcttcat gatcctggag tcaagcgtgc attagtcgta     1560
ggagttggac ttcaaatact tcagcagttc tcaggcatca acggagttct ttactacaca     1620
ccgcaaatcc ttgagcaggc gggtgtcggg atcctactat cgaacatggg gattagttct     1680
tcctcagcat ccttacttat aagtgcattg acaacccttg tgatgttacc tgcaatagct     1740
gttgcaatga ggctcatgga tctttctggt cgaaggacct tgcttctcac cacgatacca     1800
atcctgatag catctctatt ggttttagta atctcaaatc ttgttcacat gaacagcatt     1860
gtgcacgcgg tcttatcaac cgtaagcgtt gtgctctact tctgcttctt cgtgatgggt     1920
ttcggtcctg ctccaaacat cctctgttca gagattttc caactcgagt ccgcggaatc     1980
tgcatcgcca tctgcgcact caccttctgg atctgtgaca taatcgtcac ttacagtctc     2040
cccgtgctgc tcaaatccat tggactagct ggtgtgtttg aatgtacgc aatcgtatgt     2100
tgcatttcat gggtctttgt gttcattaaa gtcccggaaa ctaaaggcat gccacttgaa     2160
gtcatcacag agttcttttc tgttggagct agacaagctg aagctgctaa aaacgagtga     2220
```

<210> SEQ ID NO 13
<211> LENGTH: 737
<212> TYPE: PRT
<213> ORGANISM: Arabidopsis thaliana

<400> SEQUENCE: 13

Met Arg Ser Val Val Leu Val Ala Leu Ala Ala Ala Ile Gly Asn Met

-continued

```
1               5                   10                  15
Leu Gln Gly Trp Asp Asn Ala Thr Ile Ala Gly Ala Val Ile Tyr Ile
                20                  25                  30
Lys Lys Glu Phe His Leu Glu Lys Glu Pro Lys Ile Glu Gly Leu Ile
                35                  40                  45
Val Ala Met Ser Leu Ile Gly Ala Thr Leu Ile Thr Thr Phe Ser Gly
                50                  55                  60
Pro Val Ser Asp Lys Val Gly Arg Arg Ser Met Leu Ile Leu Ser Ser
65                  70                  75                  80
Val Leu Tyr Phe Leu Ser Ser Ile Val Met Phe Trp Ser Pro Asn Val
                85                  90                  95
Tyr Val Leu Leu Phe Ala Arg Leu Leu Asp Gly Phe Gly Ile Gly Leu
                100                 105                 110
Ala Val Thr Leu Val Pro Ile Tyr Ile Ser Glu Thr Ala Pro Ser Glu
                115                 120                 125
Ile Arg Gly Leu Leu Asn Thr Phe Pro Gln Phe Cys Gly Ser Gly Gly
                130                 135                 140
Met Phe Leu Ser Tyr Cys Leu Val Phe Gly Met Ser Leu Gln Glu Ser
145                 150                 155                 160
Pro Ser Trp Arg Leu Met Leu Gly Val Leu Ser Ile Pro Ser Ile Ala
                165                 170                 175
Tyr Phe Val Leu Ala Ala Phe Phe Leu Pro Glu Ser Pro Arg Trp Leu
                180                 185                 190
Val Ser Lys Gly Arg Met Asp Glu Ala Arg Gln Val Leu Gln Arg Leu
                195                 200                 205
Arg Gly Arg Glu Asp Val Ser Gly Glu Leu Ala Leu Leu Val Glu Gly
                210                 215                 220
Leu Gly Val Gly Lys Asp Thr Ser Ile Glu Glu Tyr Val Ile Gly Pro
225                 230                 235                 240
Asp Asn Glu Glu Asn Glu Gly Gly Asn Glu Leu Pro Arg Lys Asp Gln
                245                 250                 255
Ile Lys Leu Tyr Gly Pro Glu Asp Gly Gln Ser Trp Met Ala Lys Pro
                260                 265                 270
Val Lys Gly Gln Ser Ser Leu Ala Leu Ala Ser Arg Gln Gly Ser Met
                275                 280                 285
Leu Pro Arg Gly Gly Ser Leu Met Asp Pro Leu Val Thr Leu Phe Gly
                290                 295                 300
Ser Ile His Glu Asn Leu Pro Ser Glu Asn Met Asn Ala Ser Ser Arg
305                 310                 315                 320
Ser Met Leu Phe Pro Asn Met Gly Ser Ile Leu Gly Met Met Gly Arg
                325                 330                 335
Gln Glu Ser Gln Trp Asp Pro Glu Arg Asn Asn Glu Asp Ser Ser Asp
                340                 345                 350
Gln Asp Glu Asn Leu Asn Ser Pro Leu Leu Ser Pro Gln Thr Thr Glu
                355                 360                 365
Pro Asp Asp Tyr His Gln Arg Thr Val Gly Thr Met His Arg Arg Gln
                370                 375                 380
Ser Ser Leu Phe Met Ala Asn Val Gly Glu Thr Ala Thr Ala Thr Ser
385                 390                 395                 400
Ile Gly Gly Gly Trp Gln Leu Ala Trp Lys Tyr Asn Asp Lys Val Gly
                405                 410                 415
Ala Asp Gly Lys Arg Val Asn Gly Gly Leu Gln Arg Met Tyr Ile His
                420                 425                 430
```

```
Glu Glu Thr Ala Asn Asn Thr Asn Asn Ile Pro Phe Ser Arg Arg
        435                 440                 445

Gly Ser Leu Leu Ser Phe His Pro Glu Gly Asp Gly His Asp Gln Val
    450                 455                 460

Asn Gly Tyr Val Gln Ala Ala Leu Val Ser Gln Ala Ser Met Met
465                 470                 475                 480

Pro Gly Gly Lys Gly Glu Thr Ala Met Leu Pro Lys Glu Val Lys Asp
                485                 490                 495

Gly Pro Gly Trp Arg Glu Leu Lys Glu Pro Gly Val Lys Arg Ala Leu
            500                 505                 510

Met Val Gly Val Gly Leu Gln Ile Leu Gln Gln Phe Ala Gly Ile Asn
        515                 520                 525

Gly Val Met Tyr Tyr Thr Pro Gln Ile Leu Glu Glu Thr Gly Val Ser
    530                 535                 540

Ser Leu Leu Thr Asn Leu Gly Ile Ser Ala Glu Ser Ala Ser Leu Leu
545                 550                 555                 560

Ile Ser Ala Leu Thr Thr Leu Leu Met Leu Pro Cys Ile Leu Val Ser
                565                 570                 575

Met Arg Leu Met Asp Val Thr Gly Arg Arg Ser Leu Met Leu Ser Thr
            580                 585                 590

Ile Pro Ile Leu Ile Leu Ser Leu Val Thr Leu Val Ile Gly Ser Leu
        595                 600                 605

Val Asn Leu Gly Gly Ser Ile Asn Ala Leu Ile Ser Thr Ala Ser Val
    610                 615                 620

Thr Val Tyr Leu Ser Cys Phe Val Met Gly Phe Gly Ala Ile Pro Asn
625                 630                 635                 640

Ile Leu Cys Ser Glu Ile Phe Pro Thr Ser Val Arg Gly Leu Cys Ile
                645                 650                 655

Thr Ile Cys Ala Leu Thr Phe Trp Ile Cys Asp Ile Ile Val Thr Tyr
            660                 665                 670

Thr Leu Pro Val Met Leu Lys Ser Ile Gly Ile Ala Gly Val Phe Gly
        675                 680                 685

Ile Tyr Ala Ile Val Cys Ala Val Ala Trp Val Phe Val Tyr Leu Lys
    690                 695                 700

Val Pro Glu Thr Lys Gly Met Pro Leu Glu Val Ile Ser Glu Phe Phe
705                 710                 715                 720

Ser Val Gly Ala Lys Gln Gln Asp Ala Ala Ala Ser Phe Leu Ser Asp
                725                 730                 735

Gly

<210> SEQ ID NO 14
<211> LENGTH: 2190
<212> TYPE: DNA
<213> ORGANISM: Arabidopsis thaliana

<400> SEQUENCE: 14
atgaggagtg tagtgcttgt tgctttagcc gctgcgatag gaatatgtt gcagggctgg      60 gacaatgcca ccattgcagg agctgtaatt tacattaaga aagaatttca tttggagaaa    120
gaaccaaaga tagaaggact gatcgtggca atgtctctca ttggagccac tttgatcaca    180
actttctctg gtcctgtctc tgacaaagta ggaaggcgat caatgcttat actctcctct    240
gttctctatt tctgagtag cattgttatg ttttggtctc ccaatgtcta cgttctcctt    300
ttcgcaaggc ttcttgatgg ttttgggatc ggtttagctg tcactctcgt cccaatctac    360
```

```
atctctgaga ccgcaccttc tgagatcaga ggattactca acactttccc gcagttttgt    420
ggatccggtg ggatgttttt gtcgtattgt cttgtgtttg ggatgtcgct tcaagaatca    480
ccaagctgga ggctgatgct tggtgttttg tcaattccgt ccattgccta ctttgtactt    540
gcggctttct tcttgcctga atctccaagg tggcttgtca gcaaaggccg tatggatgaa    600
gctagacagg ttctgcagag actccgtggc agagaagatg tttcaggcga gcttgctctg    660
ctggttgaag gcttgggggt gggaaaagac acgtcgatag aagaatatgt gattggacca    720
gacaacgagg aaaacgaggg tggaaatgaa ctgccgagga agatcagat aaaactatat     780 ggtccagagg atggacagtc atggatggct aagccagtga aggacagag ttctctcgca     840 ttggcttccc gacaaggcag catgttaccg cgtggcggat ccctcatgga cccacttgtc    900
actctctttg gtagcattca tgagaatctc ccttccgaga acatgaacgc atcatcccgc    960
agcatgctct tccccaatat gggaagtata ctgggaatga tgggaaggca ggagtcccag   1020
tgggatccag agagaaacaa tgaagatagt tctgaccaag atgaaaactt aaacagtcct   1080
ctgctttctc cgcaaaccac tgagccggat gactaccacc agcggaccgt tggtaccatg   1140
cataggcgac agagcagctt gtttatggca acgtgggtg agacagcgac ggctacaagc    1200
ataggcggtg gatggcaatt ggcgtggaag tataatgaca aggttggtgc agatggtaag   1260
agagtcaatg gagggttaca gagaatgtat attcacgagg aaaccgccaa caacaacacc   1320
aacaacattc cttttttcgcg acgtggatca cttctctcct tccacccaga gggtgatggt   1380
catgatcagg tgaatggata cgttcaggct gctgcacttg tgagccaagc ttcgatgatg   1440
ccaggaggta aggcgagac cgcaatgttg ccaaaggagg ttaaggatgg tccaggctgg    1500
agggagctga agaaccagg ggttaagaga gctttgatgg ttggagttgg gcttcagata    1560
ctgcaacagt ttgcaggaat aaatggagtg atgtattata cacctcaaat attggaagaa   1620
acaggtgtgt caagtctttt gacaaaacctt ggaataagtg cagagtctgc atcgcttctc   1680
ataagcgcct taaccacact cttgatgctt ccctgcattc ttgtctccat gaggtctctg   1740
atgctttcga ctatccccat tctaatactg tcgctggtaa cactggtgat aggaagctta   1800
gtgaatcttg gaggttcaat aaacgcgttg atatcgacag caagtgttac ggtgtaccta   1860
agctgtttcg tgatgggttt tggggcaatt ccaaacatcc tctgctcaga gatattccct   1920
acttctgtgc gcggtctctg catcaccata tgtgccctca ctttctggat ctgtgacata   1980
atcgtcactt acactctccc agtcatgctc aaatccattg gcatcgcagg agtctttggc   2040
atttatgcaa tcgtctgtgc tgtcgcgtgg gtttttgtgt acctcaaggt accagagaca   2100
aagggaatgc cccttgaagt tatctctgag ttcttctccg tcggtgcaaa acagcaagac   2160
gctgcagctt catttctctc tgatggatga                                    2190
```

<210> SEQ ID NO 15
<211> LENGTH: 49
<212> TYPE: DNA
<213> ORGANISM: Artificial Sequence
<220> FEATURE:
<223> OTHER INFORMATION: 5-primer for the PCR amplification of the
       nucleotide sequence encoding Beta vulgaris tonoplast sugar
       transport protein 1

<400> SEQUENCE: 15
ggggacaagt ttgtacaaaa aagcaggctt aatgaagggt gctgtgctt                 49

<210> SEQ ID NO 16

```
<211> LENGTH: 48
<212> TYPE: DNA
<213> ORGANISM: Artificial Sequence
<220> FEATURE:
<223> OTHER INFORMATION: 3-primer for the PCR amplification of the
      nucleotide sequence encoding Beta vulgaris tonoplast sugar
      transport protein 1

<400> SEQUENCE: 16
ggggaccact ttgtacaaga aagctgggta ctccgcctta gcggcttc                    48

<210> SEQ ID NO 17
<211> LENGTH: 25
<212> TYPE: DNA
<213> ORGANISM: Artificial Sequence
<220> FEATURE:
<223> OTHER INFORMATION: 5-primer for the PCR amplification of the
      nucleotide sequence encoding Beta vulgaris tonoplast sugar
      transport protein 2.1

<400> SEQUENCE: 17
ctcgagatga gtgcagcagt attag                                             25

<210> SEQ ID NO 18
<211> LENGTH: 27
<212> TYPE: DNA
<213> ORGANISM: Artificial Sequence
<220> FEATURE:
<223> OTHER INFORMATION: 3-primer for the PCR amplification of the
      nucleotide sequence encoding Beta vulgaris tonoplast sugar
      transport protein 2.1

<400> SEQUENCE: 18
tctagagtgg cttgcttgtc ttgcacc                                           27

<210> SEQ ID NO 19
<211> LENGTH: 23
<212> TYPE: DNA
<213> ORGANISM: Artificial Sequence
<220> FEATURE:
<223> OTHER INFORMATION: 5-primer for the quantitative PCR reaction for
      the amplification of a fragment of a nucleic acid molecule
      encoding Beta vulgaris tonoplast sugar transport protein 1

<400> SEQUENCE: 19
gctgttgcta tgaggctcat gga                                               23

<210> SEQ ID NO 20
<211> LENGTH: 25
<212> TYPE: DNA
<213> ORGANISM: Artificial Sequence
<220> FEATURE:
<223> OTHER INFORMATION: 3-primer for the quantitative PCR reaction for
      the amplification of a fragment of a nucleic acid molecule
      encoding Beta vulgaris tonoplast sugar transport protein 1

<400> SEQUENCE: 20
ccttagcggc ttctaactgt ttagg                                             25

<210> SEQ ID NO 21
<211> LENGTH: 23
<212> TYPE: DNA
<213> ORGANISM: Artificial Sequence
<220> FEATURE:
<223> OTHER INFORMATION: 5-primer for the quantitative PCR reaction for
      the amplification of a fragment of a nucleic acid molecule
      encoding Beta vulgaris tonoplast sugar transport protein 2.1

<400> SEQUENCE: 21
```
aaagatgaac accactgtgt atg                                           23

<210> SEQ ID NO 22
<211> LENGTH: 24
<212> TYPE: DNA
<213> ORGANISM: Artificial Sequence
<220> FEATURE:
<223> OTHER INFORMATION: 3-primer for the quantitative PCR reaction for
      the amplification of a fragment of a nucleic acid molecule
      encoding Beta vulgaris tonoplast sugar transport protein 2.1

<400> SEQUENCE: 22
gtcatcagtg gcttgcttgt cttg                                          24

<210> SEQ ID NO 23
<211> LENGTH: 23
<212> TYPE: DNA
<213> ORGANISM: Artificial Sequence
<220> FEATURE:
<223> OTHER INFORMATION: 5-primer for the quantitative PCR reaction for
      the amplification of a fragment of a nucleic acid molecule
      encoding Beta vulgaris tonoplast sugar transport protein 2.2

<400> SEQUENCE: 23
aaagatgagc actactgtgc acg                                           23

<210> SEQ ID NO 24
<211> LENGTH: 24
<212> TYPE: DNA
<213> ORGANISM: Artificial Sequence
<220> FEATURE:
<223> OTHER INFORMATION: 3-primer for the quantitative PCR reaction for
      the amplification of a fragment of a nucleic acid molecule
      encoding Beta vulgaris tonoplast sugar transport protein 2.2

<400> SEQUENCE: 24
tcagttgtcc ttgtcttcag aagg                                          24

<210> SEQ ID NO 25
<211> LENGTH: 24
<212> TYPE: DNA
<213> ORGANISM: Artificial Sequence
<220> FEATURE:
<223> OTHER INFORMATION: 5-primer for the quantitative PCR reaction for
      the amplification of a fragment of a nucleic acid molecule
      encoding Beta vulgaris tonoplast sugar transport protein 3

<400> SEQUENCE: 25
tctacttctg ctgctttgtc atgg                                          24

<210> SEQ ID NO 26
<211> LENGTH: 22
<212> TYPE: DNA
<213> ORGANISM: Artificial Sequence
<220> FEATURE:
<223> OTHER INFORMATION: 3-primer for the quantitative PCR reaction for
      the amplification of a fragment of a nucleic acid molecule
      encoding Beta vulgaris tonoplast sugar transport protein 3

<400> SEQUENCE: 26
tcagcttcag cttgccttgc ac                                            22

<210> SEQ ID NO 27
<211> LENGTH: 23
<212> TYPE: DNA
<213> ORGANISM: Artificial Sequence
<220> FEATURE:

<223> OTHER INFORMATION: 5-primer for the quantitative PCR reaction for
the amplification of a fragment of a nucleic acid molecule
encoding Beta vulgaris elongation factor 1 alpha 1

<400> SEQUENCE: 27
ccacattgct gtcaagtttg ctg         23

<210> SEQ ID NO 28
<211> LENGTH: 21
<212> TYPE: DNA
<213> ORGANISM: Artificial Sequence
<220> FEATURE:
<223> OTHER INFORMATION: 3-primer for the quantitative PCR reaction for
the amplification of a fragment of a nucleic acid molecule
encoding Beta vulgaris elongation factor 1 alpha 1

<400> SEQUENCE: 28
tggtaacctt ggcaccggtt g         21

<210> SEQ ID NO 29
<211> LENGTH: 8
<212> TYPE: PRT
<213> ORGANISM: Unknown
<220> FEATURE:
<223> OTHER INFORMATION: Prosite Pattern PS00216

<400> SEQUENCE: 29

Leu Ile Val Met Ser Thr Ala Gly
1               5

<210> SEQ ID NO 30
<211> LENGTH: 8
<212> TYPE: PRT
<213> ORGANISM: Unknown
<220> FEATURE:
<223> OTHER INFORMATION: Prosite Pattern PS00216

<400> SEQUENCE: 30

Leu Ile Val Met Phe Ser Ala Gly
1               5

<210> SEQ ID NO 31
<211> LENGTH: 6
<212> TYPE: PRT
<213> ORGANISM: Unknown
<220> FEATURE:
<223> OTHER INFORMATION: Prosite Pattern PS00216

<400> SEQUENCE: 31

Leu Ile Val Met Ser Ala
1               5

<210> SEQ ID NO 32
<211> LENGTH: 8
<212> TYPE: PRT
<213> ORGANISM: Unknown
<220> FEATURE:
<223> OTHER INFORMATION: Prosite Pattern PS00216

<400> SEQUENCE: 32

Leu Ile Val Met Phe Tyr Trp Ala
1               5

<210> SEQ ID NO 33
<211> LENGTH: 4
<212> TYPE: PRT
<213> ORGANISM: Unknown

<220> FEATURE:
<223> OTHER INFORMATION: Prosite PAttern PS00216

<400> SEQUENCE: 33

Gly Ser Thr Ala
1